(12) United States Patent
Arand et al.

(10) Patent No.: US 7,096,060 B2
(45) Date of Patent: Aug. 22, 2006

(54) METHOD AND SYSTEM FOR DETECTION OF HEART SOUNDS

(75) Inventors: Patricia Arand, McMinnville, OR (US); David Lynn Burton, McMinnville, OR (US)

(73) Assignee: Innovise Medical, Inc., Portland, OR (US)

( * ) Notice: Subject to any disclaimer, the term of this patent is extended or adjusted under 35 U.S.C. 154(b) by 209 days.

(21) Appl. No.: 10/607,845

(22) Filed: Jun. 27, 2003

(65) Prior Publication Data

US 2004/0267148 A1    Dec. 30, 2004

(51) Int. Cl.
*A61B 5/0402*    (2006.01)
(52) U.S. Cl. .................... 600/513; 600/528
(58) Field of Classification Search ............ 600/528, 600/521, 513; 607/44
See application file for complete search history.

(56) References Cited

U.S. PATENT DOCUMENTS

| | | | | |
|---|---|---|---|---|
| 3,799,147 A | * | 3/1974 | Adolph et al. | 600/513 |
| 4,905,706 A | * | 3/1990 | Duff et al. | 600/514 |
| 6,409,675 B1 | * | 6/2002 | Turcott | 600/508 |
| 6,438,196 B1 | * | 8/2002 | Cesmeli | 378/8 |
| 6,643,548 B1 | * | 11/2003 | Mai et al. | 607/17 |
| 6,869,404 B1 | * | 3/2005 | Schulhauser et al. | 600/528 |
| 2004/0260188 A1 | * | 12/2004 | Syed et al. | 600/509 |

* cited by examiner

*Primary Examiner*—Angela D. Sykes
*Assistant Examiner*—Alyssa M. Alter
(74) *Attorney, Agent, or Firm*—Jon M. Dickinson PC; Robert D. Varitz PC

(57) ABSTRACT

A method and system for automatically detecting heart sounds. The sound system receives sound data corresponding to beats of the heart. The sound system analyzes the sound data to detect the presence of a heart sound within the beats. The sound system then outputs an indication of the heart sounds that were detected. The sound system may use ECG data to identify various locations (e.g., R peak) within a beat and use those locations to assist in the detection of heart sounds.

10 Claims, 20 Drawing Sheets

METHOD AND SYSTEM FOR DETECTION OF HEART SOUNDS

TECHNICAL FIELD

The described technology relates to detecting heart sounds.

BACKGROUND

Four sounds may be generated during each heartbeat. The sounds are produced by blood turbulence and vibration of cardiac structures due primarily to the closing of the valves within the heart. These four sounds are identified as S1, S2, S3, and S4. S1 is usually the loudest heart sound and is the first heart sound during ventricular contraction. S1 is often described as a "lubb" sound. S1 occurs at the beginning of ventricular systole and relates to the closure of the atrioventricular valves between the atria and the ventricles. S2 is often described as a "dubb" sound. S2 occurs at the beginning of the diastole and relates to the closing of the semilunar valves separating the aorta and pulmonary artery from the left and right ventricles, respectively. S1 and S2 can be easily heard with a stethoscope ("normal heart sounds"). S3 and S4, however, can usually not be heard in the normal heart ("abnormal heart sounds") of a person over 40 years old. S3, also referred to as "ventricular gallop," occurs in the early diastolic period and is caused by the ventricular wall distending to the point it reaches its elastic limit. S4, also referred to as "atrial gallop," occurs near the end of atrial contraction and is also caused by the ventricular wall distending until it reaches its elastic limit.

Heart sounds can be used to augment the diagnosis and to help assess the severity of important types of cardiac disease. For example, after age 40, S3 can indicate congestive heart failure, and S4 can indicate hypertension, acute myocardial infarction, or coronary artery disease. Unfortunately, recent studies have shown that even highly experienced physicians do not reliably detect important heart sounds.

The electrocardiogram ("ECG") is an important tool for monitoring heart activity and diagnosing heart conditions. The ECG is a recording of the electrical activity of the heart. This electrical activity causes the heart to contract. The contraction in turn causes blood to be pumped throughout the body. This electrical activity is spontaneously generated. As the cells within the heart change from a negative potential to a positive potential (depolarization), the muscles within the heart contract. Conversely, when the cells change from a positive to a negative potential (repolarization), the muscles return to their noncontracted state. The periodic contraction of the heart causes the pumping action. This spontaneous electrical activity typically occurs about once a second. By analyzing a patient's ECG, various cardiac abnormalities, such as ischemia, can be detected.

DETAILED DESCRIPTION

A method and system for automatically detecting heart sounds is provided. In one embodiment, the sound system receives sound data corresponding to beats of the heart. The sound system analyzes the sound data to detect the presence of a particular heart sound within the beats. The heart sounds may include S1, S2, S3, and S4. The sound system then outputs an indication of the heart sounds that were detected. The sound system may use ECG data to identify various locations (e.g., R peak) within a beat and use those locations to assist in the detection of heart sounds. The sound system in one embodiment filters the sound data into various frequency bands. The sound system defines the frequency bands to assist in the analysis of heart sounds whose expected frequency is within one or more of the bands. The sound system may also filter the sound data to reduce the effects of transient or spurious data or out-of-band noise. The sound system identifies temporal windows in which each sound is expected to be located. For example, one window is defined for S1, and another window is defined for S4. The sound system analyzes the filtered and processed sound data to detect the presence of S3 and S4. (The sound system in one embodiment assumes S1 and S2 are always present.) If the data within the window meets certain conditions, then the presence of the corresponding sound is indicated. In the case of S3 and S4, the system may categorize each beat as not, possibly, or probably having the sound. The sound system then indicates the presence of S3 or S4 based on how many beats are categorized as possibly or probably having that sound. In one embodiment, the sound system analyzes multiple beats to indicate the presence and location of the heart sounds. Alternatively, the sound system may analyze an "average" beat (e.g., when uncorrelated noise is high). The sound system then identifies the location of the geometric centroid of the sound signal as the location of the corresponding sound. The sound system may also perform noise analysis to determine whether the noise level is such that the heart sounds cannot be reliably detected. The sound system may output a sound graph that displays the sound data for a beat along with an indication of the heart sounds whose presence has been indicated. The sound graph may identify the location of each sound within the beat. In this way, heart sounds can be reliably detected and be used to augment the diagnosis of and assess the severity of cardiac disease.

Figure 1:
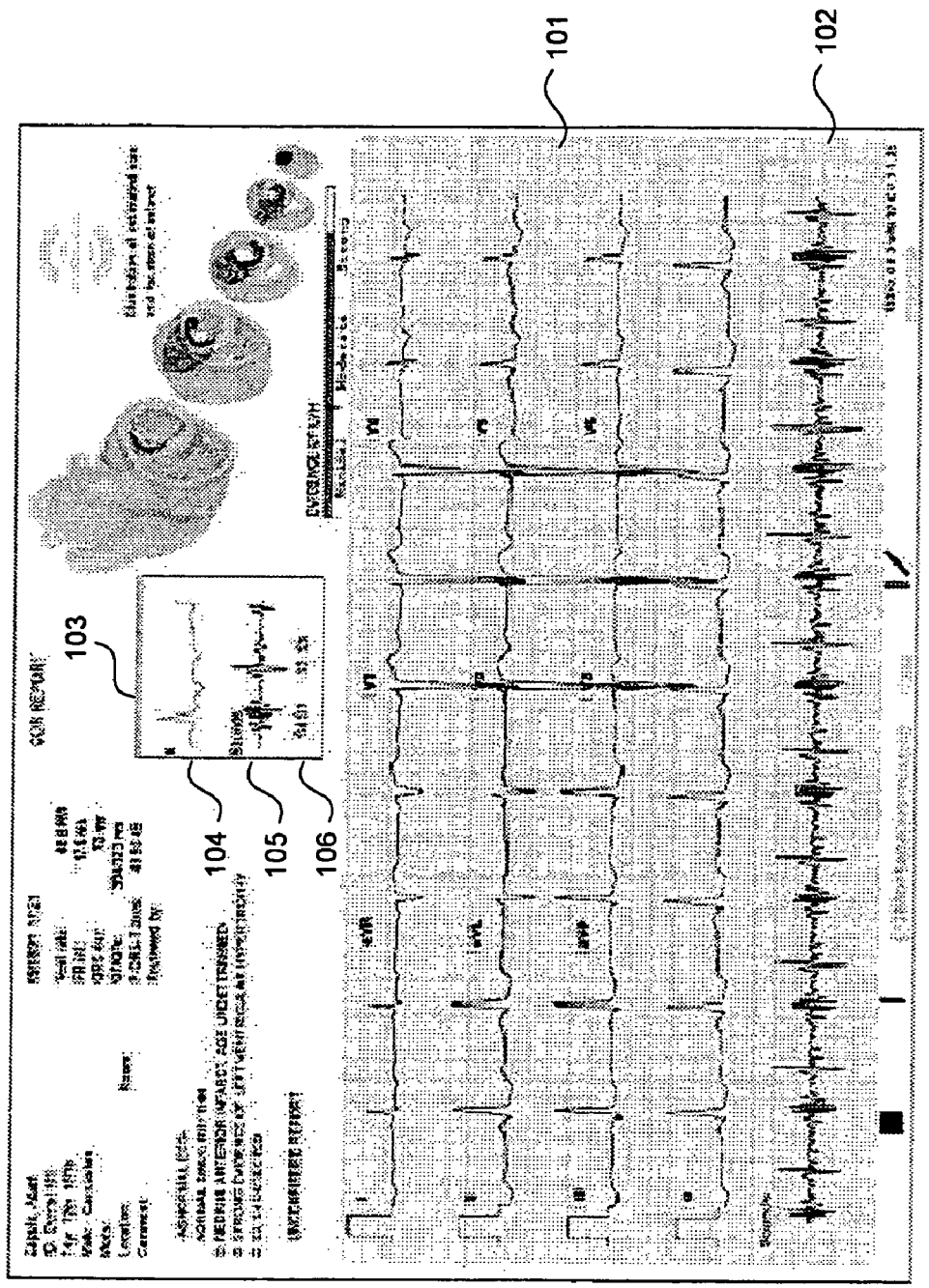
FIG. 1 is an ECG diagram illustrating detection of heart sounds.

FIG. 1 is an ECG diagram illustrating detection of heart sounds. The diagram includes a conventional ECG graph 101 and a sound graph 102. The sound graph represents the amplitude of the sound detected by a sound sensor that in one embodiment is placed at the ECG electrode V4 location. (See U.S. patent application Ser. No. 10/461,732, entitled "Real-Time, Sound-Quality Competitive, Single-Site From Plural-Site Anatomical Signal Selections" filed on Jun. 13, 2003, which is incorporated herein by reference). A sound detection area 103 includes an ECG graph 104 and a sound graph 105. The data in the sound detection area represents just over one heartbeat of data. A heart sound identification area 106 labels each of the heart sounds on the corresponding sound graph data. In this example, S4 is followed by S1, S2, S3, and S4. The labels identify both the existence and location of the corresponding sound.

Figure 2:
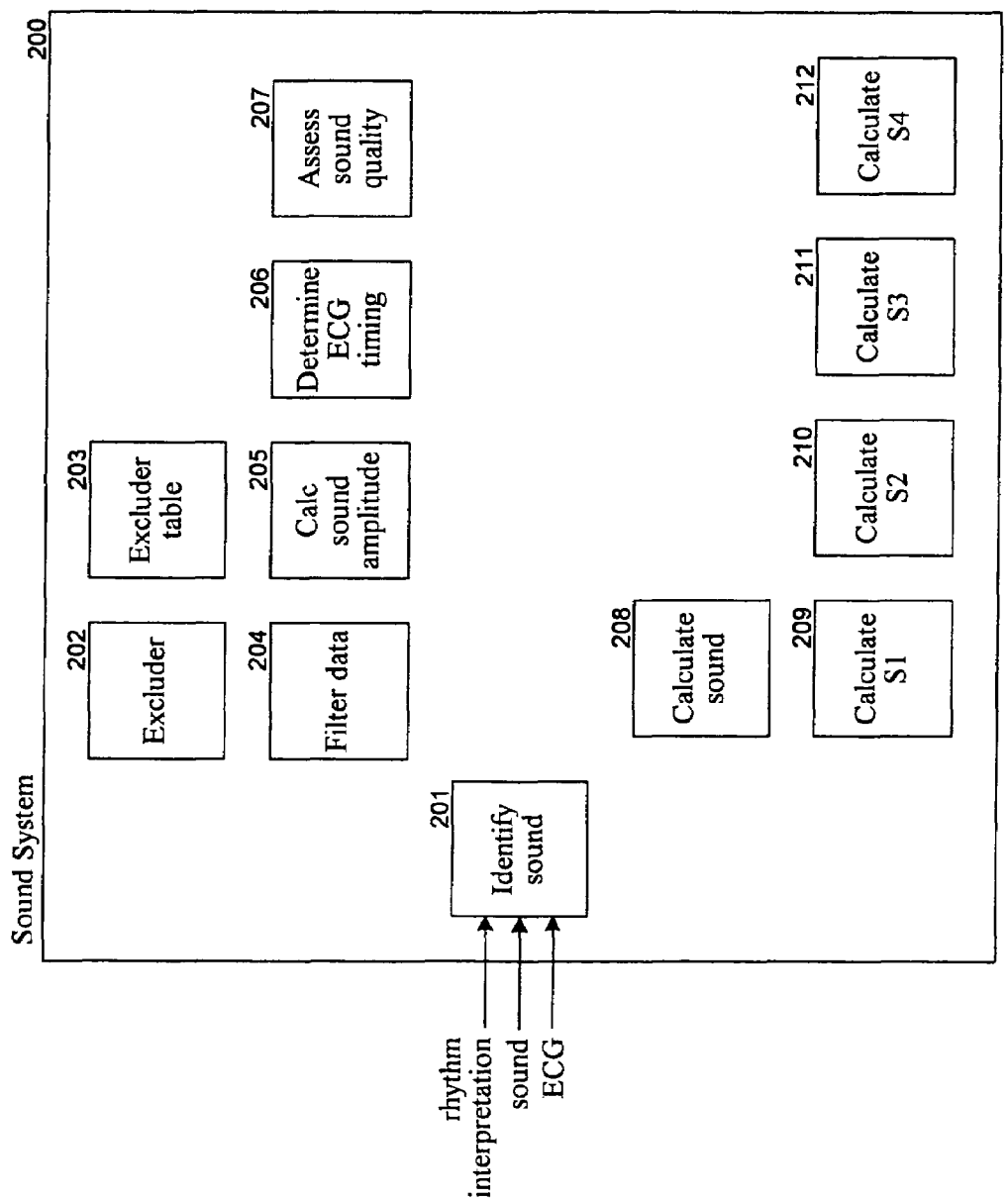
FIG. 2 is a block diagram illustrating components of the sound system in one embodiment.

FIG. 2 is a block diagram illustrating components of the sound system in one embodiment. The sound system 200 includes an identify sound component 201, an excluder component 202, an excluder table 203, a filter data component 204, a calculate sound amplitude component 205, a determine ECG timing component 206, an assess sound quality component 207, a calculate sound component 208, a calculate S1 component 209, a calculate S2 component 210, a calculate S3 component 211, and a calculate S4 component 212. The identify sound component receives rhythm interpretation data, sound data, and ECG data. The sound data is stored as an array of amplitude readings measured at the sound sampling rate. Each sound sample is identified by its location within the array. The rhythm interpretation data may identify various points within the ECG data, such as the R-wave locations. The excluder component analyzes the rhythm interpretation data to determine if any of the excluder conditions identified in the excluder table have been met. If so, the sound system may not be able to reliably identify certain sounds for that patient. The filter data component filters the sound data into various frequency bands and the ECG data into one frequency band. The calculate sound amplitude component uses root-mean-square (RMS) functions to calculate the sound amplitude in each band. The calculated amplitude is the result of the integration of multiple peaks and is a unipolar measure of the amplitude. The amplitude is calculated using a narrow RMS window and separately using a wide RMS window. The wide RMS window is used to identify the general area that contains a sound, and the narrow RMS window is used to identify the positions of the sound signals. The determine ECG timing component determines the heart rate, R—R interval, and Q-onset. The assess sound quality component determines the noise floor of each frequency band and the beat-to-beat correlation of the beats. This is used to adjust the detection sensitivity and qualify detections to reduce false detections caused by poor signal quality. If the quality is too poor, then further detection of the heart sounds may be aborted.

The calculate sound component invokes the calculate S1 component, the calculate S2 component, the calculate S3 component, and the calculate S4 component to detect and locate the sounds. The calculate S1 component identifies the location of S1 using one of bands 2, 3, or 4. The calculate S1 component identifies the band with the best signal-to-noise floor ratio for use in identifying the location of S1. The calculate S1 component assumes that the S1 location is constant for a given patient and condition during data acquisition. The calculate S1 component calculates an average distance (i.e., number of sound samples) between the R peak to the maximum amplitude within a window in which S1 is expected to be (i.e., "S1 window"). The system uses the location of the maximum amplitude as an approximation of the location of the S1 geometric centroid of the sound signal. The calculate S2 component works in a similar manner except with a different window (i.e., "S2 window"). The calculate S3 component detects whether each beat has an S3. If S3 is detected in enough beats, the component indicates the S3 was detected and identifies the location of S3. The calculate S3 component first identifies a window in which S3 is expected to be found starting at an offset from S2 and extending for a certain time interval (i.e., "S3 window"). The component then determines a ratio of the maximum amplitude within the S3 window to the median amplitude within the S1 window or S2 window for each beat. The component uses that ratio along with beat-to-beat correlation and signal-to-noise floor information to identify whether each beat has S3. In one embodiment, the system categorizes each beat as not, possibly, or probably having an S3. The system categorizes each beat by comparing the ratios for bands 1, 2, and 3 to thresholds for that band. The system uses different threshold ratios based on the beat-to-beat correlation and amount of noise in the sound data. For example, a lower threshold can be used when the beat-to-beat correlation is high and the amount of noise is low. The system indicates that S3 is detected based on how many beats are identified as possibly or probably having S3. The system then identifies the geometric centroid of S3 within bands 1 and 2 of each beat as the location of the sound signal. The system sets the location of S3 for each beat to the average of the centroids in these bands. The calculate S4 component works in the similar manner except with a different window (i.e., "S4 window").

The sound system may be implemented on a computer that includes a central processing unit, memory, input devices (e.g., keyboard and pointing devices), output devices (e.g., display devices), and storage devices (e.g., disk drives). The memory and storage devices are computer-readable media that may contain instructions that implement the sound system. The sound system may be a stand-alone system or may be integrated into a conventional ECG monitoring system.

The sound system might not attempt to detect heart sounds when various patient conditions are present because it might not be able to reliably detect the heart sounds. These "excluder" conditions might include when a patient is less than 18 years old, has a pacemaker, has atrial bigeminy, and so on. One skilled in the art will appreciate that the sound system may be able to detect some of the heart sounds even when some excluder condition occurs.

Figure 3A:
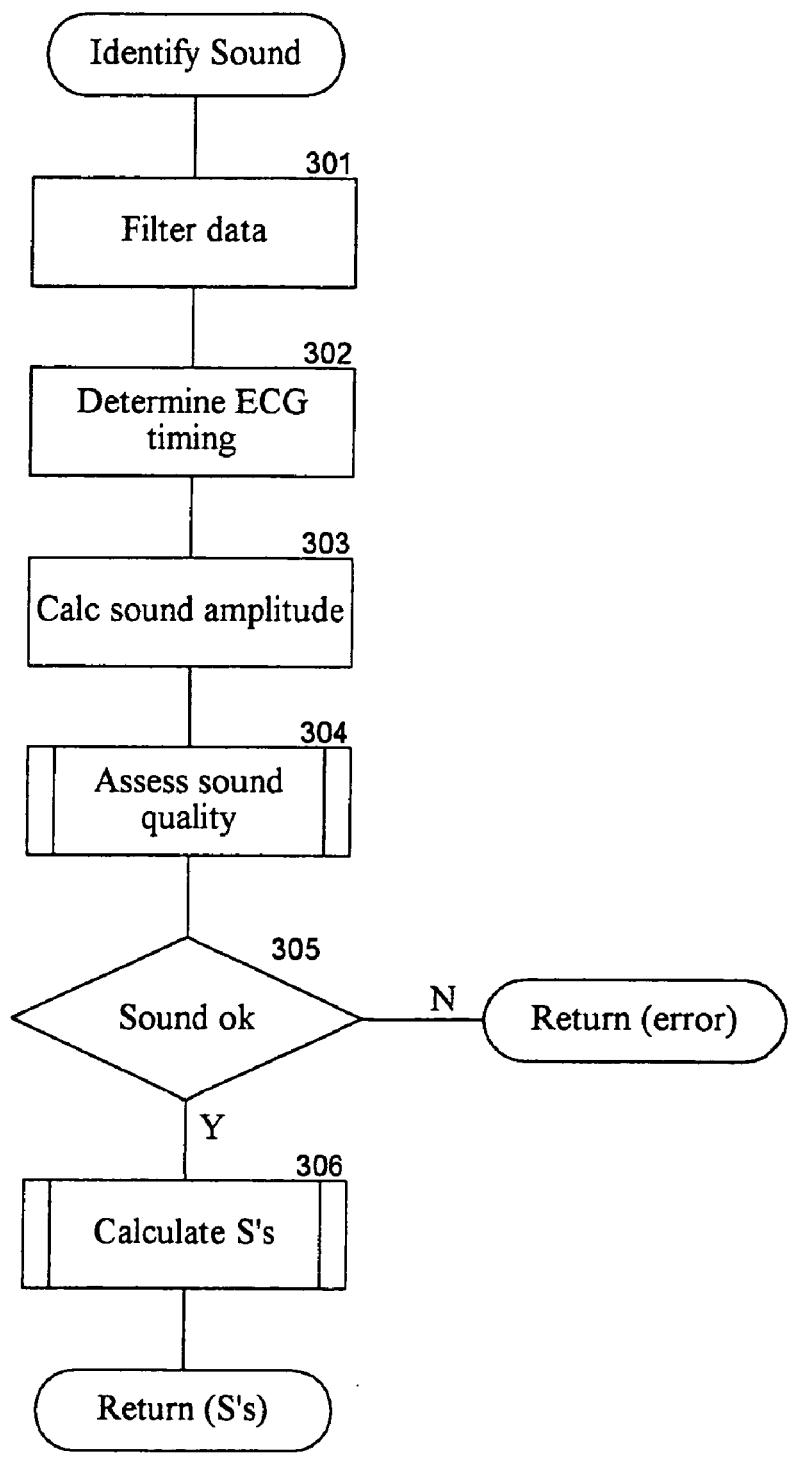
FIG. 3A is a flow diagram illustrating the processing of the identify sound component in one embodiment.

FIG. 3A is a flow diagram illustrating the processing of the identify sound component in one embodiment. This component controls the overall processing of the sound system. In block 301, the component invokes the filter data component to filter the sound data into five bands and to filter the ECG data into a single band. In block 302, the component invokes the determined ECG timing component to identify the location of various markers (e.g., Q-onset) within the ECG data. In block 303, the component invokes the calculate sound amplitude component to establish the amplitude of the sound data of each band. In block 304, the component invokes the assess sound quality component to determine the noise floor of each frequency band and the beat-to-beat correlation of the beats. In decision block 305, if the sound quality is above a minimum threshold, then the component continues at block 306, else the component returns an error. In block 306, the component invokes the calculate sound component to calculate the locations of S1 and S2 and to detect S3 and S4, if present. The component then returns the location of the sounds.

Filter Data Component

The filter data component filters the sound data into several bands and the ECG data into a single band. The filter data component first removes the DC offset from the sound and ECG data. In one embodiment, the filter data component then uses a non-causal (forward/backward) 8$^{th}$ order zero-phase Bessel bandpass filter with the following bandwidths.

| Band | Lower 3 dB point | Upper 3 dB point |
|---|---|---|
| 1 | 20 Hz | 34 Hz |
| 2 | 31 Hz | 49 Hz |
| 3 | 44 Hz | 68 Hz |
| 4 | 61 Hz | 95 Hz |
| 5 | 125 Hz | 266 Hz |
| VB | 22 Hz | 125 Hz |
| ECG | 0.5 Hz | 50 Hz |

Figure 3B:
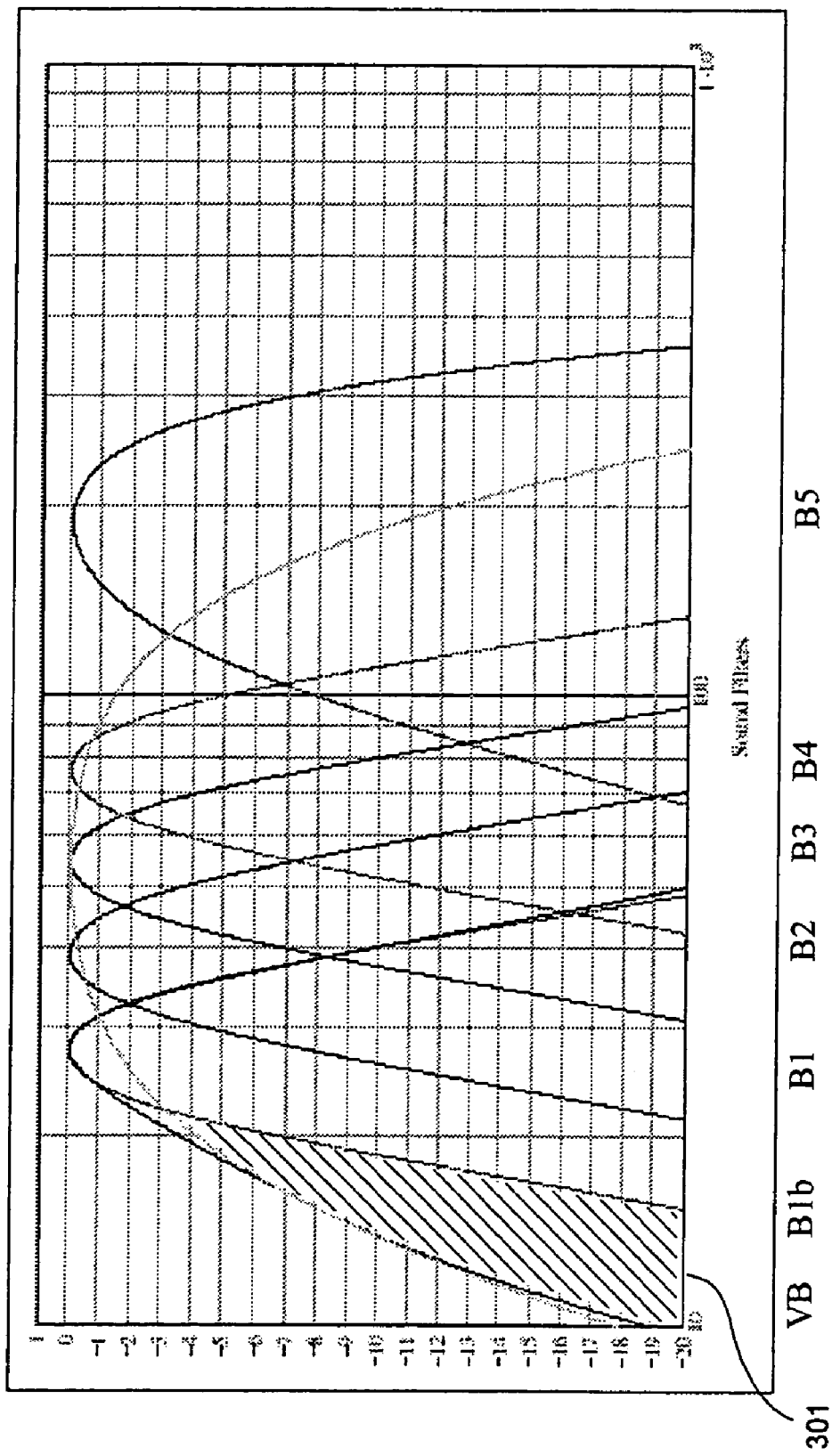
FIG. 3B is a graph illustrating the frequency response of the filters in one embodiment.

FIG. 3B is a graph illustrating the frequency response of the filters in one embodiment. The system uses bands 1–5 of the sound data to detect the sounds and uses band VB for display of sound data. In one embodiment, the specified bandwidths are not −3 dB for Bessel filters. Rather, the component uses particular Bessel parameters that result in ~−3 dB at the specification points after band pass filter form conversion and forward/backwards processing. Also, the specified bandwidths for the B1b filter are not the final result. This filter may be manually modified after generating Bessel coefficients to obtain the VB filter high pass match seen in the graph and the table. Region 301 indicates the resulting change in the B1 high pass frequency response after modification to B1b. This manual modification helps ensure that the displayed sound data is consistent with the frequencies of the analyzed bands. The component uses 2$^{nd}$ order filters. The bandpass form conversion doubles the order and forward/backwards execution doubles it again for a net filter order of 8 for each filter.

The filter data component tapers the start of the sound and ECG data with a 80 ms Blackman half window (to reduce filter startup transient effects) before executing the forward filter pass. The component then time-reverses the data. The component then again tapers and filters the data to double the attenuation characteristic and reverse the phase effects. The component finally time-reverses the data to regain the proper time order (i.e., "zero-phase forward-backward filtering").

Determine ECG Timing Component

The determine ECG timing component uses rhythm interpretation data to determine the heart rate, the R—R interval, and location of Q-onset. The component locates Q-onset by applying a derivative filtering process to the filtered ECG data. The component takes the first difference of the filtered ECG data, rectifies the data, smooths the data with a moving average window of 10 milliseconds, and then reverse-time shifts the data by 5 milliseconds to correct for phase shifting of the smoothing function. The component then calculates a global mean amplitude of the ECG data. The component then uses a 20 millisecond search window to search backwards in time from the R-wave peak location for a window whose mean amplitude is less then the global mean amplitude. The component then sets the location of Q-onset to the location of the minimum amplitude within a window that is 10 milliseconds back from the ending time of that window. One skilled in the art will appreciate that various well-known techniques may be used to identify various markers in the ECG data.

Calculate Sound Amplitude

The calculate sound amplitude component establishes the amplitude of each band, reducing the effect of transient or spurious data. The component uses an RMS function that is applied using a narrow RMS window and a wide RMS window to each band to produce two sets of processed data for each band. The following table illustrates the sizes of the narrow and wide RMS windows in one embodiment.

| Band | Narrow RMS Window | Wide RMS Window |
|---|---|---|
| 1 | 24 ms | 100 ms |
| 2 | 16 ms | 64 ms |
| 3 | 10 ms | 44 ms |
| 4 | 6 ms | 28 ms |
| 5 | 4 ms | 18 ms |

The component thus generates narrow RMS data and wide RMS data for each band. The different size windows reveal different levels of detail in the data. The window sizes are based upon wavelength and having a certain number of cycles at the frequency of interest for each band in the window. The wide RMS data is used to improve the ability to locate the S1 and S2 centroids without disturbances from short-term transient effects.

Assess Sound Quality Component

Figure 4:
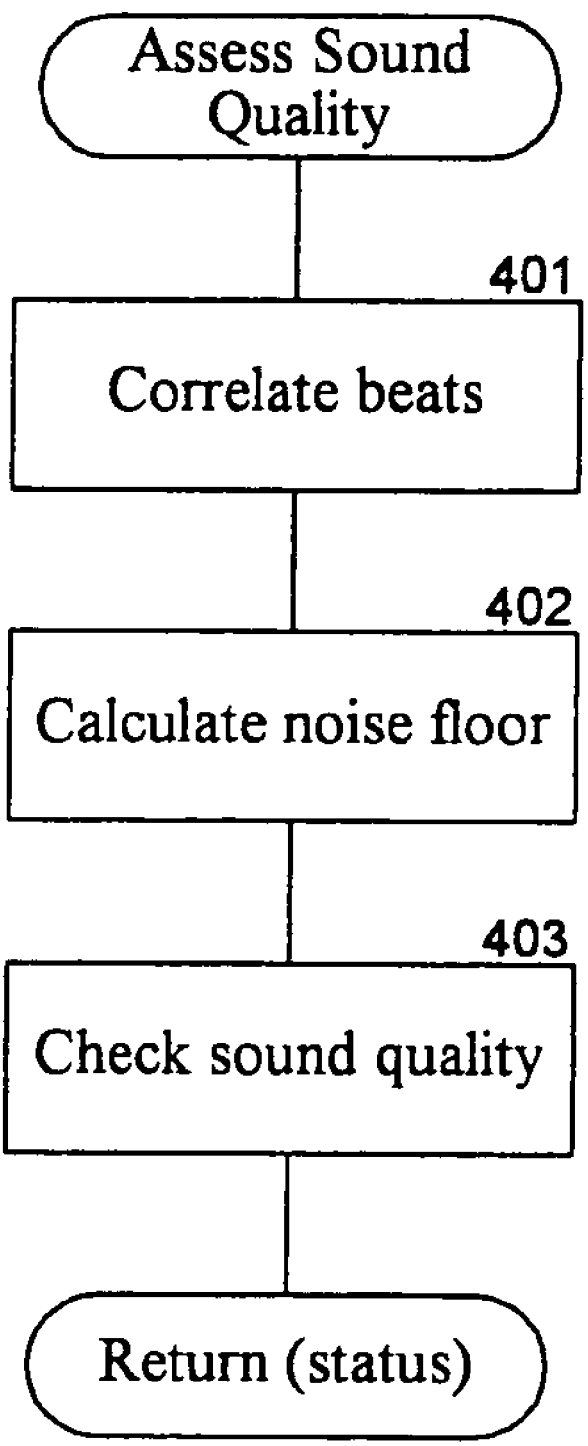
FIG. 4 is a flow diagram illustrating the processing of the assess sound quality component into one embodiment.

FIG. 4 is a flow diagram illustrating the processing of the assess sound quality component in one embodiment. The component determines the noise floor of each frequency band and the beat-to-beat correlation of each beat. In block 401, the component generates a beat-to-beat correlation for each beat in bands 1, 2, and 3 using the narrow RMS data. The component calculates two Pearson correlation coefficients for each beat. One coefficient compares with the previous beat, and the other coefficient compares with the next beat. The component then calculates a mean correlation for each band based on the correlation coefficients. The component in one embodiment uses a beat correlation window starting at the R peak minus the P-R interval and having a length of a predetermined percentage (e.g., 85%) of the median R—R interval. If the R—R interval variability is large, the individual beat length is shortened to avoid beat overlap. The individual correlation coefficients are used to classify individual beats for detection of S3 and S4. An S3 or S4 detection is rejected if the corresponding correlation coefficient is below a threshold. This condition can occur as a result of irregularity of the heart sound or contamination of the heart sound by non-cardiac signals or noise. In block 402, the component calculates a noise floor for each sound band. The component calculates an average minimum amplitude for each band. The component calculates the average amplitudes within a moving window using the narrow RMS band. The system then averages the five smallest amplitudes calculated for the moving window. In one embodiment, the window is 20% of the average R—R interval with a minimum of 100 milliseconds for bands 2, 3, 4, and 5. The window is 10% of the average R—R interval with a minimum of 50 milliseconds for band 1. In block 403, the component checks the sound quality based on the noise floor and correlation data. The following table illustrates conditions for identifying line noise, air leak, inconsistent beat, or general noise.

| Noise Type | Band 1 | | Band 2 | | Band 3 | | Band 4 | Band 5 |
| --- | --- | --- | --- | --- | --- | --- | --- | --- |
| | Noise Floor | Corr | Noise Floor | Corr | Noise Floor | Corr | Noise Floor | Noise Floor |
| Line noise (50/60 Hz) | | High | Low | | | Low | High | High |
| Air leak | | | | | | | Low | |
| Inconsistent beats | | Low | | Low | | Low | | |
| Noise | | | High | | High | | High | High |

For example, if band 1 has a high correlation, band 2 has a low noise floor, band 3 has a low correlation, and bands 4 and 5 have a high noise floor, then line noise is detected. If any of these noise types are detected, the component returns an indication of the detected condition.

Calculate Sound Components

Figure 5:
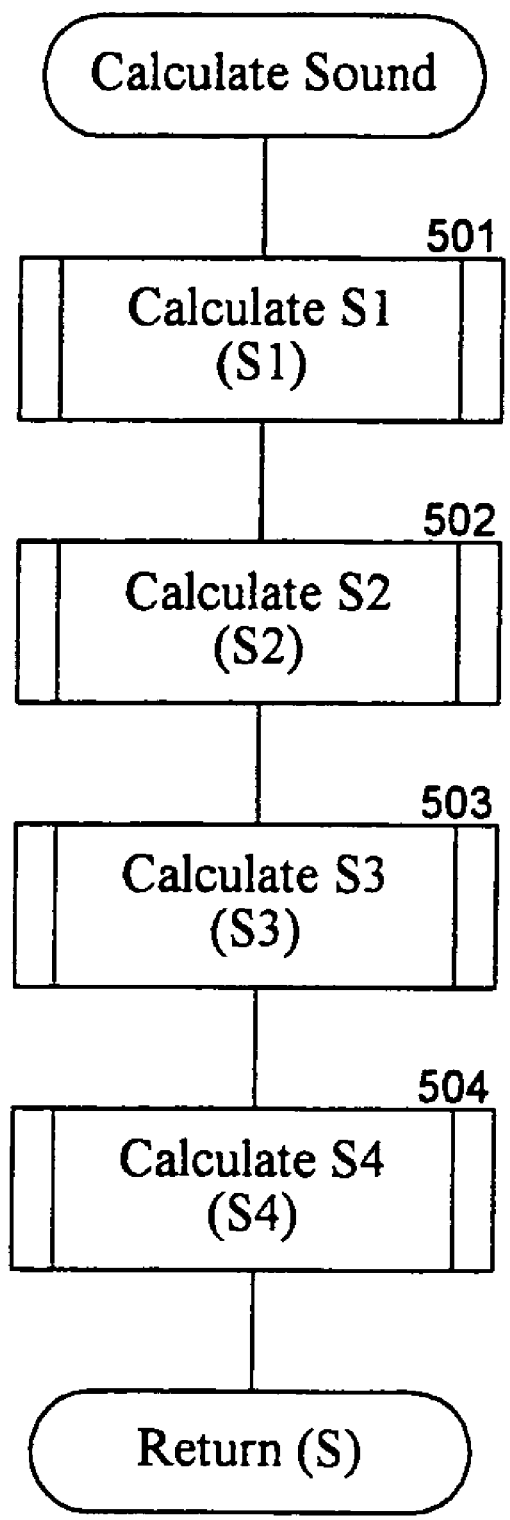
FIG. 5 is a flow diagram illustrating the processing of the calculate sound component in one embodiment.

FIG. 5 is a flow diagram illustrating the processing of the calculate sound component in one embodiment. The component detects whether S3 and S4 are present and identifies the locations of S1, S2, S3, and S4. In blocks 501–504, the component invokes the calculate S1 component, the calculate S2 component, the calculate S3 component, and the calculate S4 component. In one embodiment, the component also determines whether the S3 window and S4 window overlap to a certain extent. If so, the detected sounds are identified as "summation gallop." The component calculates the mean overlap for all beats using the non-shortened S3 window (see description of the calculate S3 component). The component then returns the location of each sound.

Figure 6:
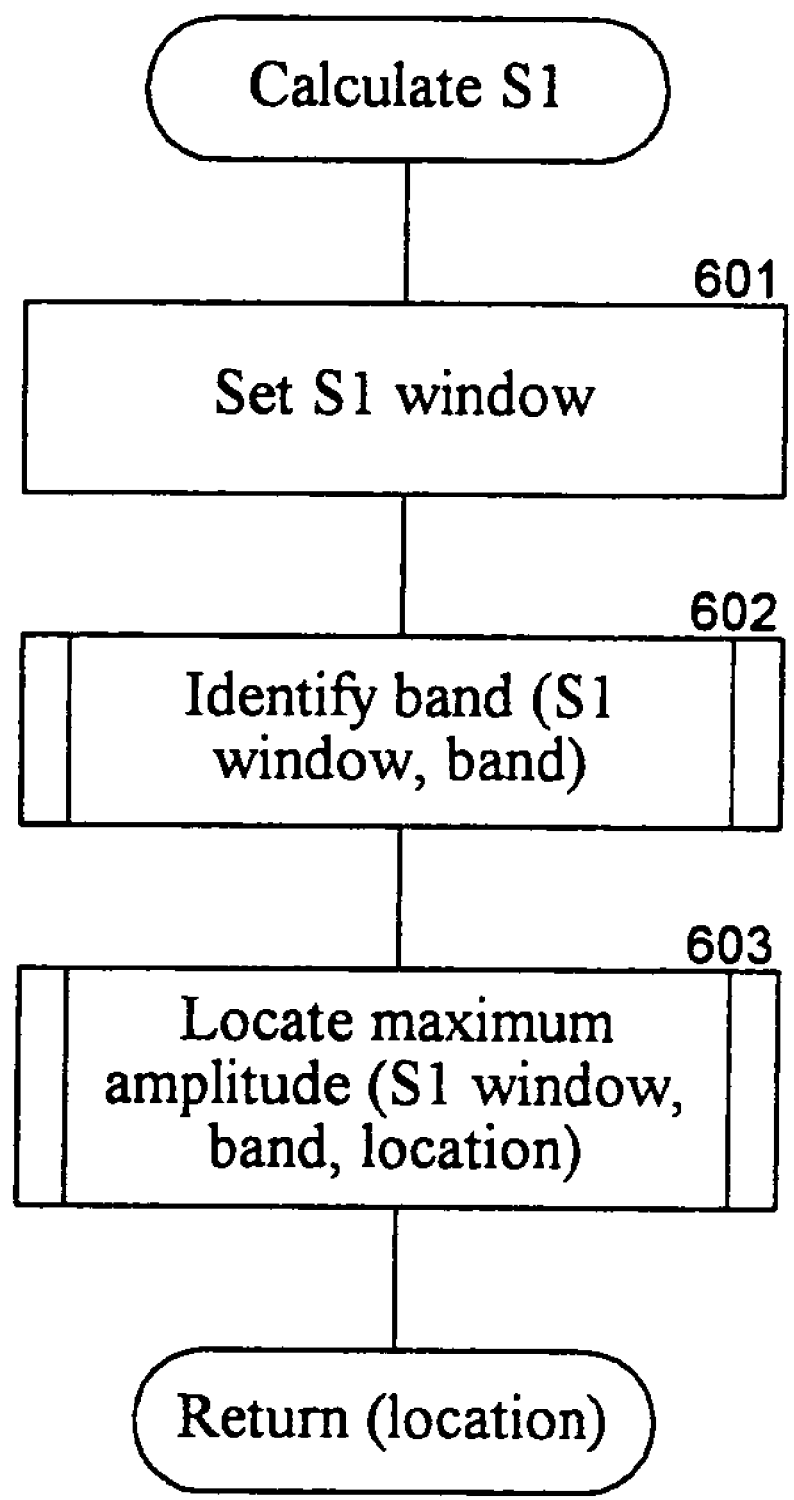
FIG. 6 is a flow diagram illustrating the processing of the calculate S1 component in one embodiment.

FIG. 6 is a flow diagram illustrating the processing of the calculate S1 component in one embodiment. The calculate S1 component identifies which of bands 2, 3, or 4 should be used to identify the location of S1 and then calculates an average time (e.g., represented by number of samples) between the R peak to the maximum amplitude within the S1 window. The maximum amplitude is an approximation of the geometric centroid of S1 and corresponds to the location of S1. In block 601, the component defines the S1 window for each beat as starting from Q-onset and extending 150 milliseconds. In block 602, the component invokes the select band component passing an indication that S1 is to be located and receiving an indication of the selected band in return. In block 603, the component invokes the locate maximum amplitude component passing an indication that S1 is being located and the selected band, and receiving the average of the maximum amplitude locations for all beats with respect to the R peak in return. The component then returns the average location as the location of S1.

Figure 7:
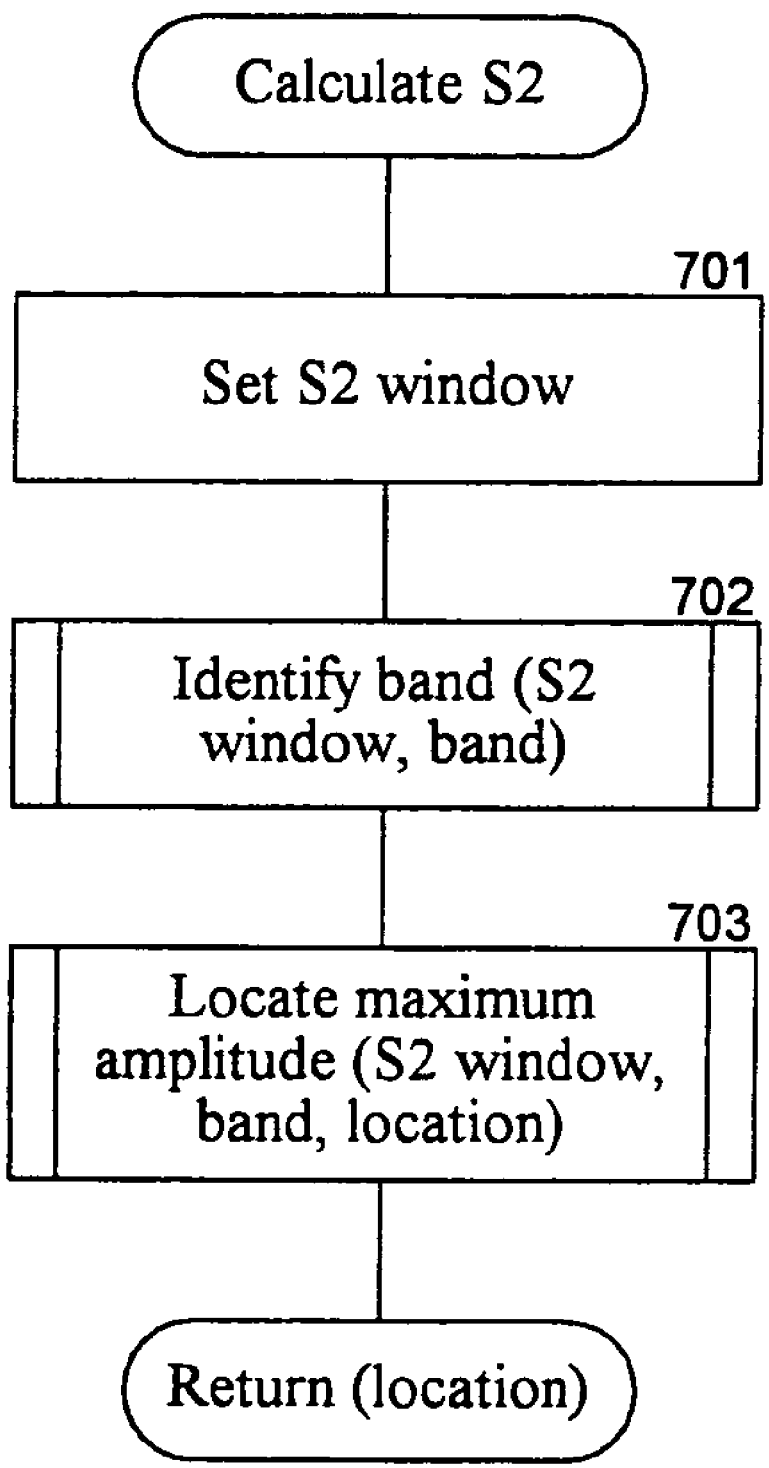
FIG. 7 is a flow diagram illustrating the processing of the calculate S2 component in one embodiment.

FIG. 7 is a flow diagram illustrating the processing of the calculate S2 component in one embodiment. The calculate S2 component identifies which of bands 2, 3, or 4 should be used to identify the location of S2 and then calculates an average time between the R peak to the maximum amplitude within the S2 window. The maximum amplitude is an approximation of the geometric centroid of S2 and corresponds to the location of S2. In block 701, the component defines the S2 window for each beat as starting at the R peak plus 12.5% of the R—R interval plus 200 milliseconds and extending for 180 milliseconds. In block 702, the component invokes the select band component passing an indication that S2 is to be located and receiving an indication of the selected band in return. In block 703, the component invokes the locate maximum amplitude component passing an indication that S2 is being located and the selected band, and receiving the average of the maximum amplitude locations for all beats with respect to the R peak in return. The component then returns the average location as the location of S2.

Figure 8:
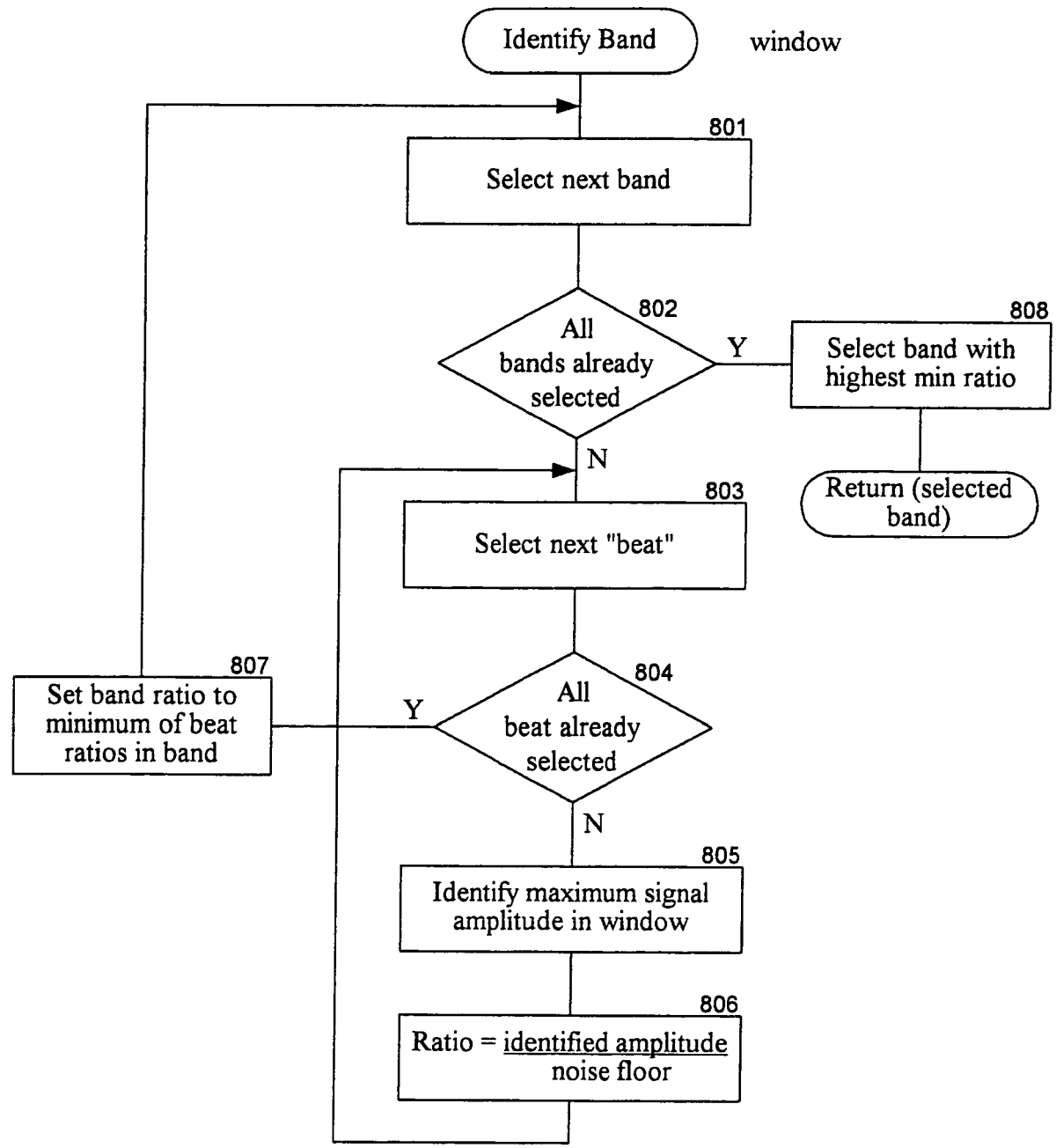
FIG. 8 is a flow diagram illustrating the processing of the identify band component in one embodiment.

FIG. 8 is a flow diagram illustrating the processing of the select band component in one embodiment. The component selects the bands that are to be used for locating S1 and S2. The component is passed an indication of the sound (i.e., S1 or S2) that is being located and selects one of bands 2, 3, or 4 to be used for locating the sound. The component identifies the maximum amplitude in the sound window (i.e., S1 window or S2 window) for each beat of bands 2, 3, and 4 using the narrow RMS data. For each band, the component takes the minimum of the maximum amplitudes and divides by the noise floor for the band to generate a signal-to-noise floor ratio for the band. The component then selects the band with the highest ratio for use in locating the sound. Conceptually, this component selects the band with the best signal-to-noise ratio. In blocks 801–807, the component loops selecting each band and each beat within each band and calculating the ratio for the band. In block 801 the component selects the next band starting with band 2. In decision block 802, if all the bands have already been selected (e.g., bands 2, 3, and 4), then the component continues at block 808, else the component continues at block 803. In block 803, the component selects the next beat within the selected band. In decision block 804, if all the beats of the selected band have already been selected, then the component continues at block 807 to set the signal-to-noise floor ratio for the selected band, else the component continues at block 805. In block 805, the component identifies the maximum amplitude within the sound window for the selected beat. In block 806, the component calculates the ratio of the maximum amplitude to the noise floor of the selected band. The component then loops to block 803 to select the next beat. In block 807, the component sets the ratio for the band to the minimum of the ratios for each beat in the selected band and loops to block 801 to select the next band. In block 808, the component selects the band with the highest signal-to-noise floor ratio and then returns an indication of that band.

Figure 9:
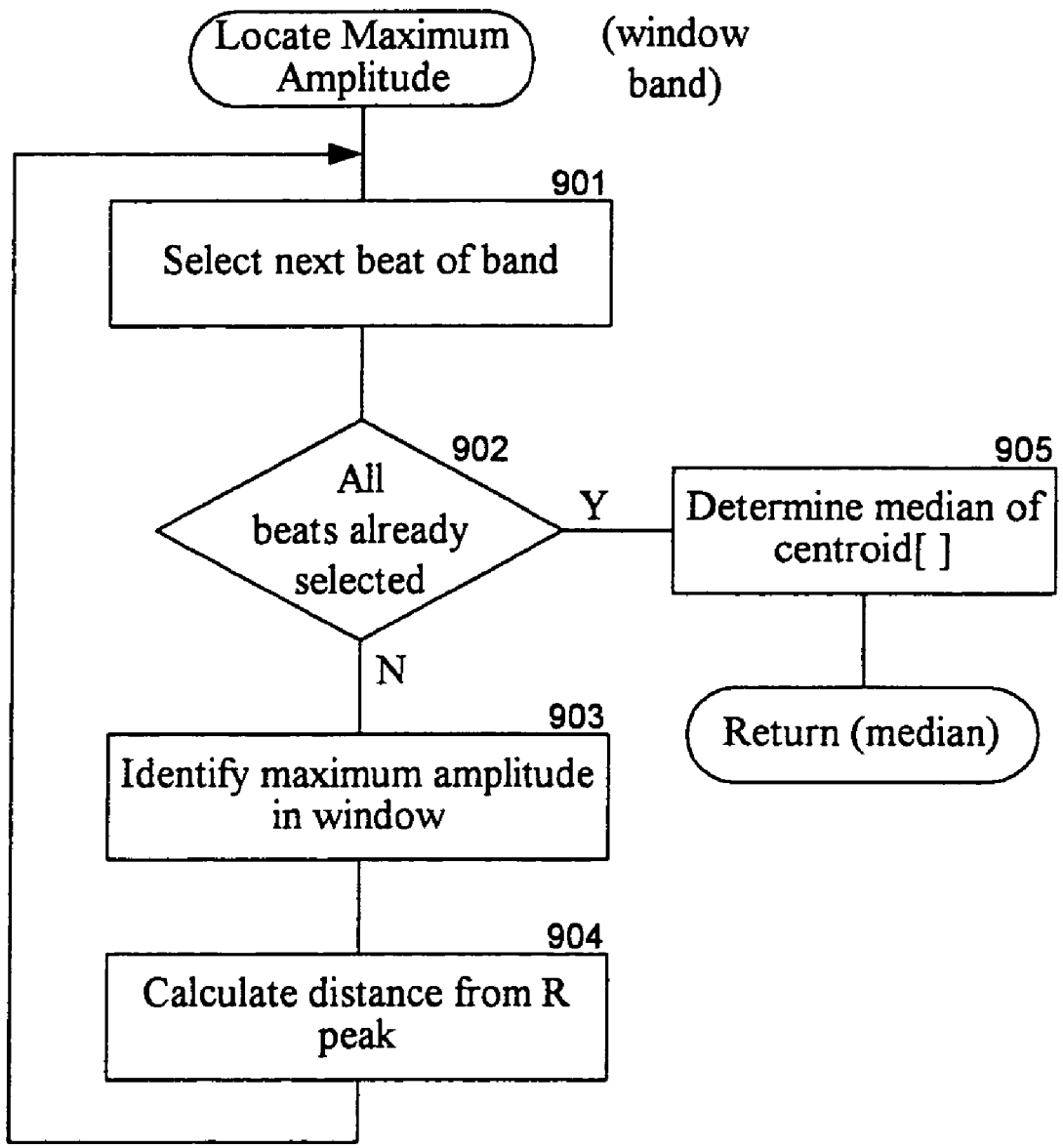
FIG. 9 is a flow diagram illustrating the processing of the calculate mean centroid component in one embodiment.

FIG. 9 is a flow diagram illustrating the processing of the locate maximum amplitude component in one embodiment. The component finds the location of the maximum amplitudes for the bands that are selected for locating S1 and S2. The component is passed an indication of the sound (i.e., S1 or S2) that is being located and a band to be used for the location and returns the median location of the maximum amplitudes. For each beat, the component finds the location of the maximum amplitude within the sound window (i.e., S1 window or S2 window) using the wide RMS data. The component then uses the median of those. locations as the location of the sound relative to the R peak in each beat. Thus, the component assumes that the sound of each beat is located at a fixed time interval from the R peak of that beat. In blocks 901–904, the component loops selecting each beat of the passed band and determining the location of the maximum amplitude. In block 901, the component selects the next beat of the passed band. In decision block 902, if all the beats of the passed band have already been selected, then the component continues at block 905, else the component continues at block 903. In block 903, the component identifies the maximum amplitude within the sound window using the wide RMS data. In block 904, the component calculates distance in samples between the R peak and the identified maximum amplitude. The component then loops to block 901 to select the next beat. In block 905, the component calculates the median of the distances and returns it as the location of the sound from the R peak.

Figure 10:
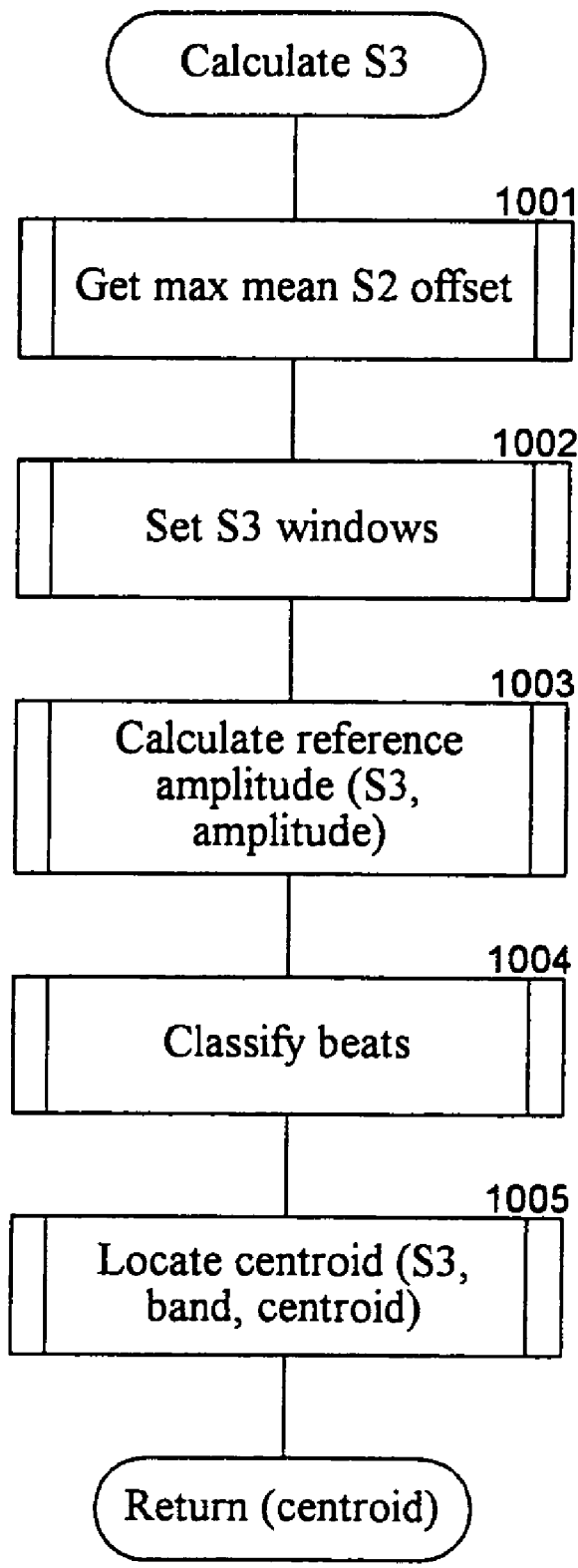
FIG. 10 is a flow diagram illustrating the processing of the calculate S3 component in one embodiment.

FIG. 10 is a flow diagram illustrating the processing of the calculate S3 component in one embodiment. The component first identifies the S3 window as starting at an offset from S2 and extending for a certain time interval (e.g., 130 milliseconds). The component determines a ratio of the maximum amplitude within the S3 window for each beat to the median amplitude within the S1, window or S2 window. The component uses that ratio along with beat-to-beat correlation and signal-to-noise information to identify whether each beat has an S3. The component then identifies the location of the geometric centroid within the S3 window of the selected band as the location of S3. In block 1001, the component invokes the get maximum median S2 offset component. The S2 offset is the start of the S3 window. In block 1002, the component invokes the set S3 windows component to set the S3 window for each beat. In block 1003, the component invokes the calculate reference amplitudes component passing an indication that S3 is being identified and receiving the reference amplitude for each band in return. In block 1004, the component invokes the classify beat component, which classifies each beat as not, possibly, or probably having an S3 based on a ratio of the amplitude of S3 to the reference amplitudes in the various bands. In block 1005, the component analyzes the classifications of beats to determine whether to indicate that an S3 has been detected. In one embodiment, the component indicates that a beat is detected when the sum of the number of probable beats plus the one-half the number of possible beats is greater than or equal to one-half the number of valid beats and is greater than or equal to three. In block 1005, the component invokes the locate centroid component passing an indication that S3 is being detected and receiving the location of the S3 centroid in return. The component then returns the location of the centroid as the location of S3.

Figure 11:
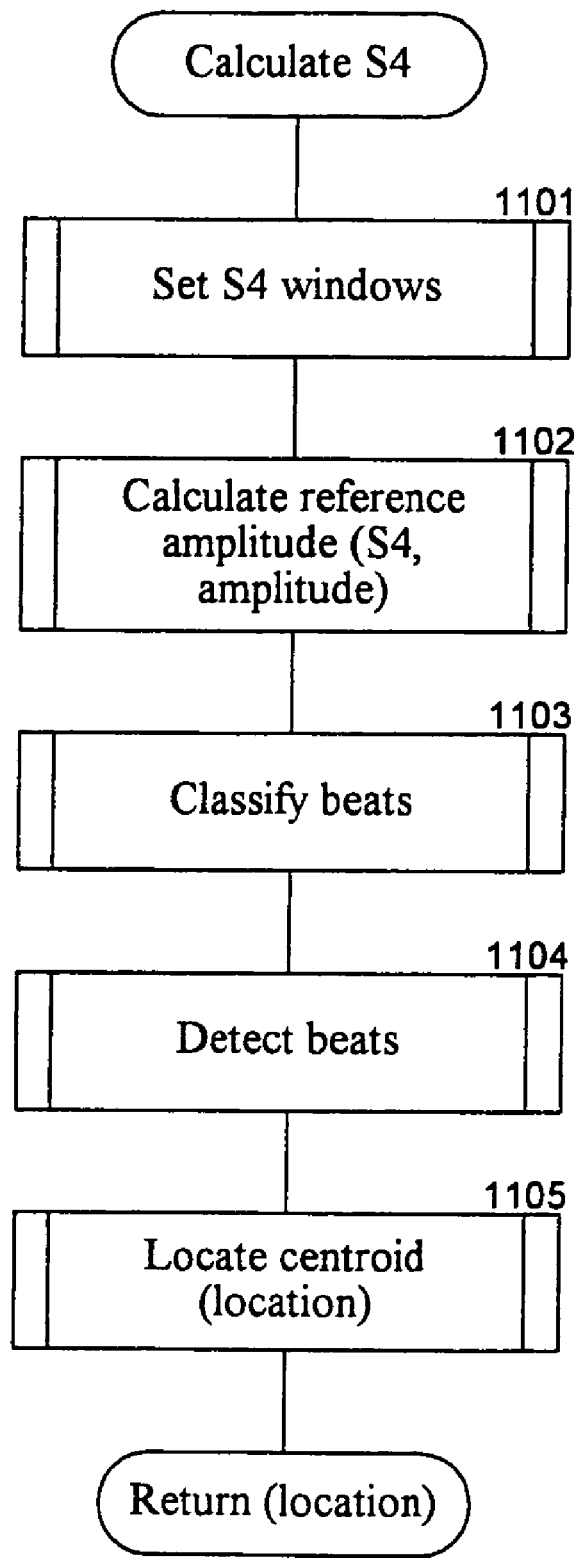
FIG. 11 is a flow diagram illustrating the processing of the calculate S4 component in one embodiment.

FIG. 11 is a flow diagram illustrating the processing of the calculate S4 component in one embodiment. The component first identifies the S4 window starting at Q-onset minus ⅔ of the P-R interval. If the P-R interval has not been identified, then ⅕ of the mean R—R interval is used instead. The S4 window extends to Q-onset minus two times the narrow RMS window size for the band. The component determines a ratio of the maximum amplitude within the S4 window for each beat to the median amplitude within the S1 window or S2 window. The component uses that ratio along with beat-to-beat correlation and signal-to-noise information to identify whether each beat has an S4. The component then identifies the geometric centroid within the S4 window as the location of S4. In block 1101, the component invokes the set S4 windows component to set the window for each beat. In block 1102, the component invokes the calculate reference amplitude component passing an indication that S4 is being identified and receiving the reference amplitude in return. In block 1103, the component invokes the classify beat component, which classifies each beat as not, possibly, or probably having an S4 based on the ratio of the amplitude of S4 to the reference amplitude in the various bands. In block 1104, the component analyzes the classifications of beats to determine whether to indicate that an S4 has been detected. In one embodiment, the component indicates that a beat is detected when the sum of the number of probable beats plus one-half the number of possible beats is greater than or equal to one-half the number of valid beats and is greater than or equal to three. In block 1105, the component invokes the locate centroid component passing an indication that S4 is to be located and the selected band, and receiving the location of the S4 centroid in return. The component then returns the location of the centroid as the location of S4.

Figure 12:
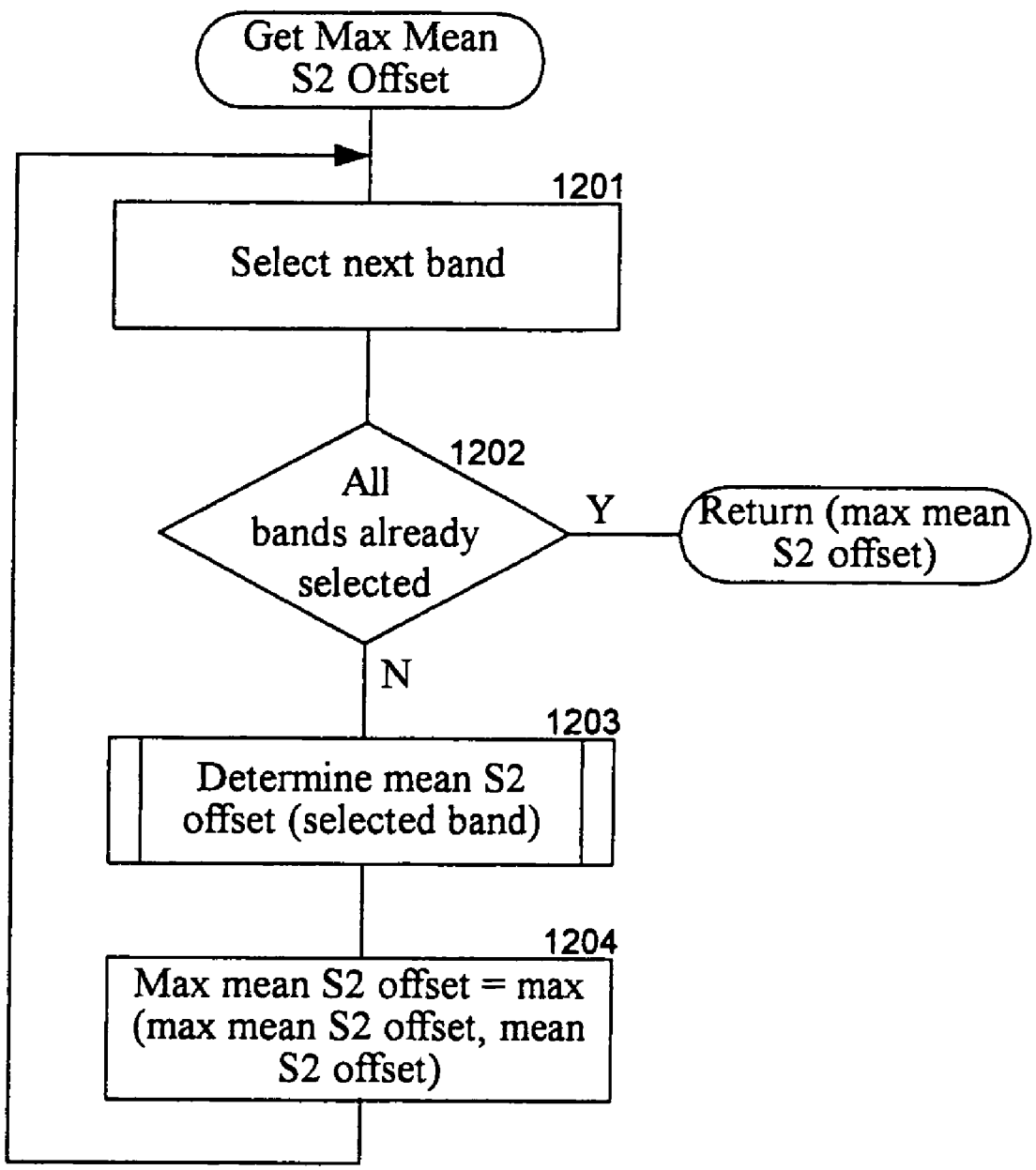
FIG. 12 is a flow diagram illustrating the processing of the get maximum mean S2 offset component in one embodiment.

FIG. 12 is a flow diagram illustrating the processing of the get maximum mean S2 offset component in one embodiment. The component determines the S2 offset for each beat. The component takes the first difference of the wide RMS data and then smooths the data with a 26 milliseconds moving average window followed by a time adjustment to avoid phase shifts. The component then calculates the second difference, smooths, and time adjusts the data. The component calculates the mean S2 offset for each band. The maximum of these mean S2 offsets for bands 1, 2, 3, and 4 is the start of the S3 window. In blocks 1201–1204, the component loops selecting each band and calculating the mean S2 offset within that band. In block 1201, the component selects the next band. In decision block 1202, if all the bands have already been selected, then the component returns the maximum mean S2 offset, else the component continues at block 1203. In block 1203, the component invokes the determine mean S2 offset component passing an indication of the selected band. In block 1204, the component sets the maximum mean S2 offset to the maximum of the mean S2 offset calculated in block 1203 and the previous maximum mean S2 offset. The component limits the maximum mean S2 offset to be within a range of 60 to 120 milliseconds of the S2 centroid. The component then loops to block 1201 to select the next band.

Figure 13:
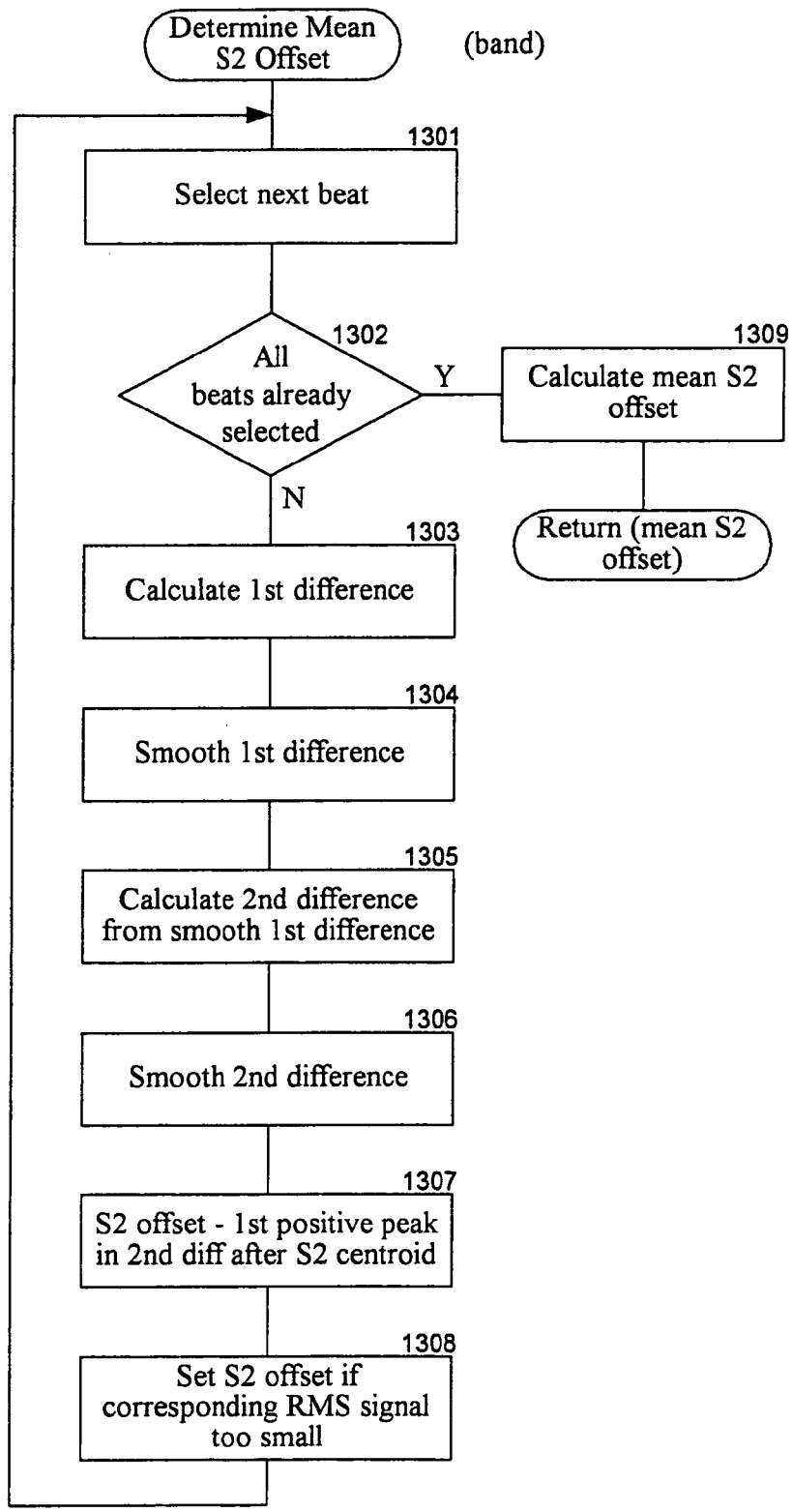
FIG. 13 is a flow diagram illustrating the processing of the determine latest mean S2 offset component in one embodiment.

FIG. 13 is a flow diagram illustrating the processing of the determine latest mean S2 offset component in one embodiment. The mean S2 offset corresponds to the start of the S3 window plus a fixed delay. The component determines the mean S2 offset for the passed band. In blocks 1301–1308, the component loops selecting each beat within the passed band and calculating its S2 offset. In block 1301, the component selects the next beat within the passed band. In decision block 1302, if all the beats within the passed band have already been selected, then the component continues at block 1309, else the component continues at block 1303. In block 1303, the component starting with the wide RMS data calculates the first difference. In block 1304, the component smooths the first difference using a 26 milliseconds moving average window. The components also adjust for phase shifts. In block 1305, the component calculates a second difference from the smoothed first difference. In block 1306, the component smooths the second difference and adjusts for phase shifts. In block 1307, the component identifies the S2 offset as the first positive peak in the second difference after S2. One skilled in the art will appreciate that many different techniques can be used to detect the location of the S2 offset, such as match filtering or different smoothing algorithms. In block 1308, the component limits the S2 offset if the corresponding RMS amplitude is too small. The component then loops to block 1301 to select the next beat within the passed band. In block 1309, the component calculates the mean of the S2 offsets for the individual beats and returns that as the mean S2 offset for the passed band.

Figure 14:
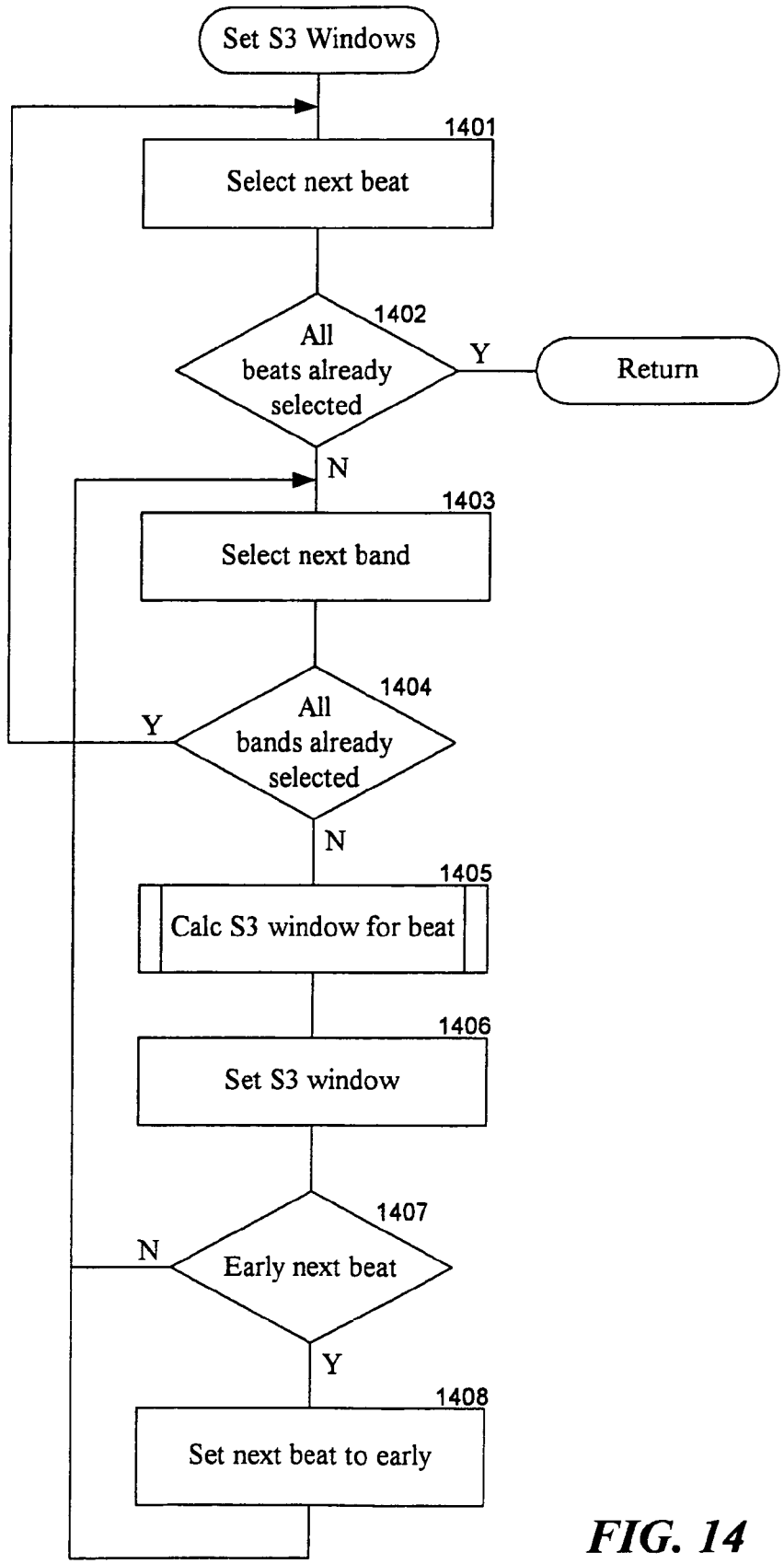
FIG. 14 is a flow diagram illustrating the processing of the set S3 windows component in one embodiment.

FIG. 14 is a flow diagram illustrating the processing of the set S3 windows component in one embodiment. The S3 window for each beat is set to start at the maximum mean S2 offset and to extend 130 milliseconds. If the S3 window overlaps Q-onset of the next beat, the component shortens the S3 window to Q-onset. If the shortening of the S3 window exceeds 50% of the S3 window, then the component labels the next beat as an early beat. In blocks 1401–1408, the component loops selecting each beat and each band for each beat and setting the S3 window for the beat. In block 1401, the component selects the next beat. In decision block 1402, if all the beats have already been selected, then the component returns, else the component continues at block 1403. In block 1403, the component selects the next band for the selected beat. In decision block 1404, if all the bands for the selected beat have already been selected, then the component loops to block 1401 to select the next beat, else the component continues at block 1405. In block 1405, the component invokes the calculate S3 window for a beat component. In block 1406, the component sets the S3 window for the selected beat. In decision block 1407, if the next beat is early, then the component continues at block 1408, else the component loops to block 1401 to select the next beat. In block 1408, the component sets an indication that the next beat is early and loops to block 1401 to select the next beat.

Figure 15:
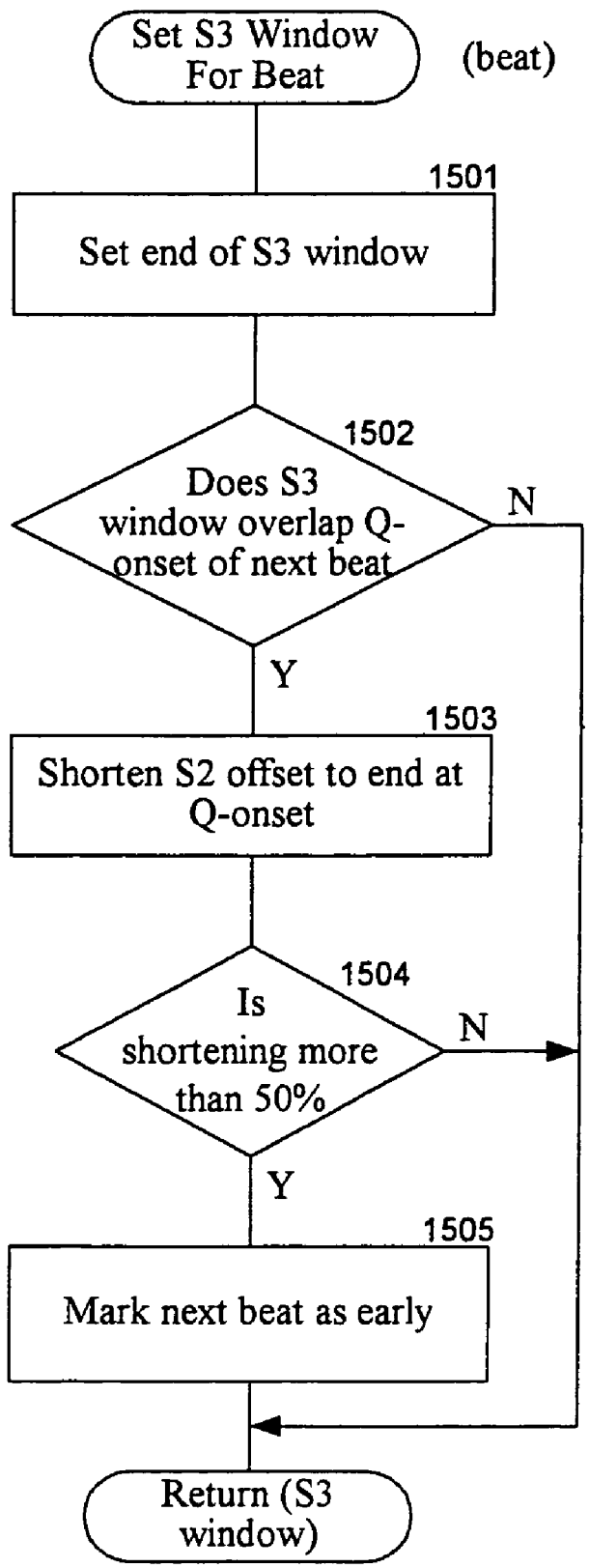
FIG. 15 is a flow diagram illustrating the processing of the set S3 window for a beat component in one embodiment.

FIG. 15 is a flow diagram illustrating the processing of the set S3 window for a beat component in one embodiment. The component defines the S3 window to start at the maximum mean S2 offset and to extend for 130 milliseconds. If, however, the S3 window overlaps Q-onset of the next beat, the S3 window is shortened to the Q-onset. If the shortening exceeds 50%, then the next beat is labeled as an early beat. In block 1501, the component sets the end of the window to the window start plus 130 milliseconds. In decision block 1502, if the S3 window overlaps Q-onset of the next beat, then the component continues at block 1503, else the component returns the S3 window. In block 1503, the component shortens the S3 window to the Q-onset of the next beat. In decision block 1504, if the shortening is more than 50% of the S3 window, then the component continues at block 1505, else the component returns the S3 window. In block 1505, the component marks the next beat as early and then returns the S3 window and an indication that the next beat is early.

Figure 16:
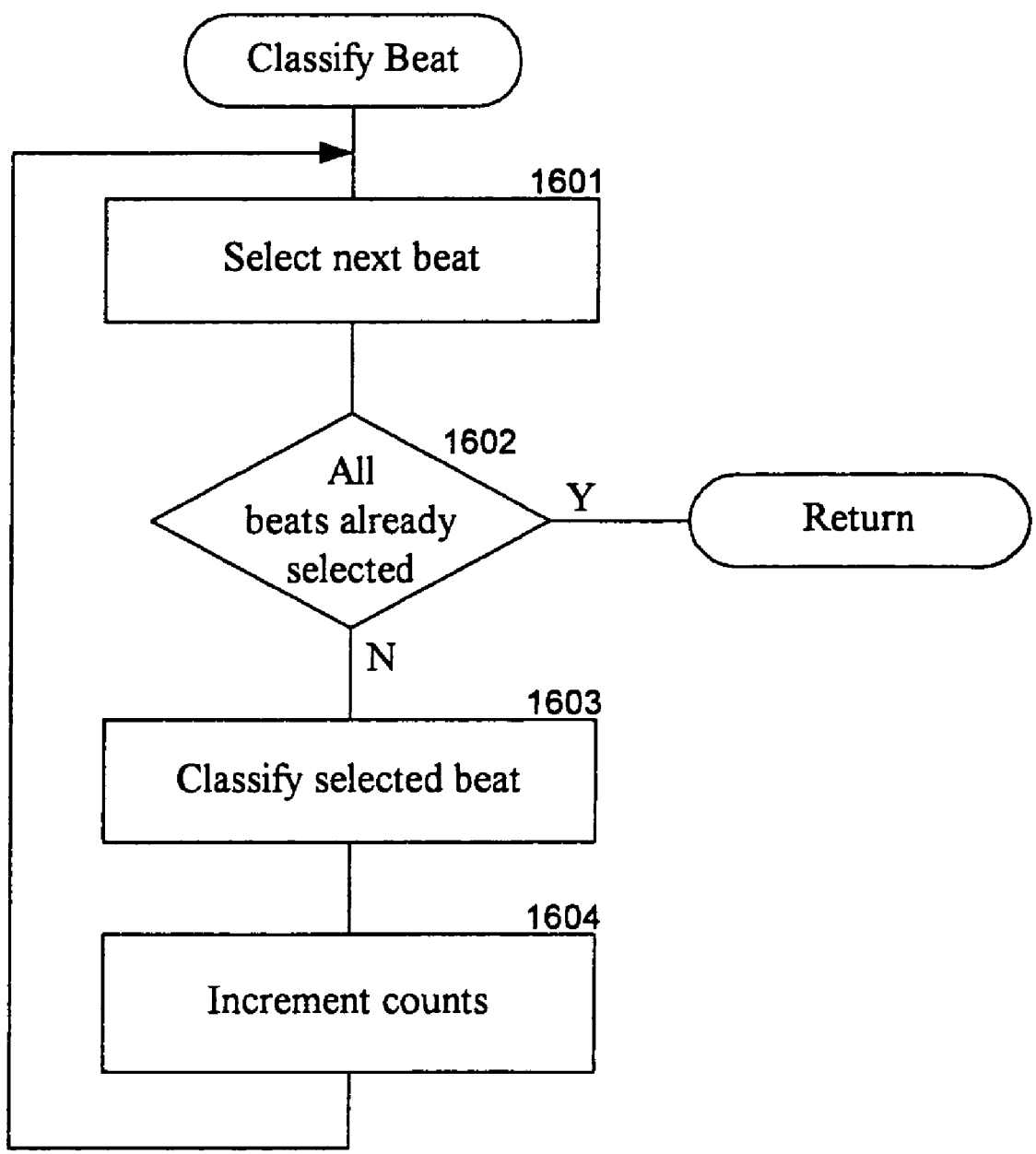
FIG. 16 is a flow diagram illustrating the processing of the select band component in one embodiment.

FIG. 16 is a flow diagram illustrating the processing of the classify beat component in one embodiment. This component is passed an indication of the sound that is to be detected (i.e., S3 or S4) and classifies each beat as not having, possibly having, or probably having the passed sound. In block 1601, the component selects the next beat. In decision block 1602, if all the beats have already been selected, then the component returns, else the component continues at block 1603. A detection is invalid when the correlation coefficient is below 0.8, the beat is an early beat for S4 detection or the next beat is an early beat for S3 detection, the sound ratio in band 5 exceeds 50%, or the beat was previously identified as abnormal by the rhythm interpretation. In block 1603, the component classifies the selected beat as an invalid beat or a beat with no sound present, possibly a sound present, or probably a sound present according to the following table:

| | Sound Ratio Threshold | | | |
|---|---|---|---|---|
| Band | Corr > 0.8 and SNFR > 3 | Corr > 0.97 and SNFR > 40 | Corr > 0.98 and SNFR > 50 | Sound Classification |
| 1 | 17% | 14.45% | 11.9% | "Possible" |
| 2 | 12% | 10.2% | 8.4% | "Possible" |
| 1 | 23% | 19.55% | 16.1% | "Probable" |
| 2 | 19% | 16.15% | 13.3% | "Probable" |
| 3 | 14% | 11.9% | 9.8% | "Probable" |

The component calculates the ratio of the amplitude of the sound (e.g., S3 or S4) within the select beat to the reference amplitude. If the ratio exceeds an applicable threshold from the table, then the beat is classified accordingly. For example, if the beat-to-beat correlation for the selected beat is 0.975 and the signal-to-noise floor ratio is 41, then for band 2 the possible threshold is 10.2% and the probable threshold is 16.15%. If the ratio is greater than 16.15%, then the beat is classified as "probable." If the ratio is between 10.2% and 16.15%, then it is classified as "possible." The component checks the ratio against all applicable thresholds. If none of the thresholds are exceeded, then no sound is detected for the beat. If at least one probable threshold is exceeded, then the beat is classified as probable. If a detection is particularly strong in any of bands 1, 2, or 3, then the component accepts it even if the correlation is low. This threshold is set as a function of the signal-to-noise floor ratio in each band. The component then returns.

Figure 17:
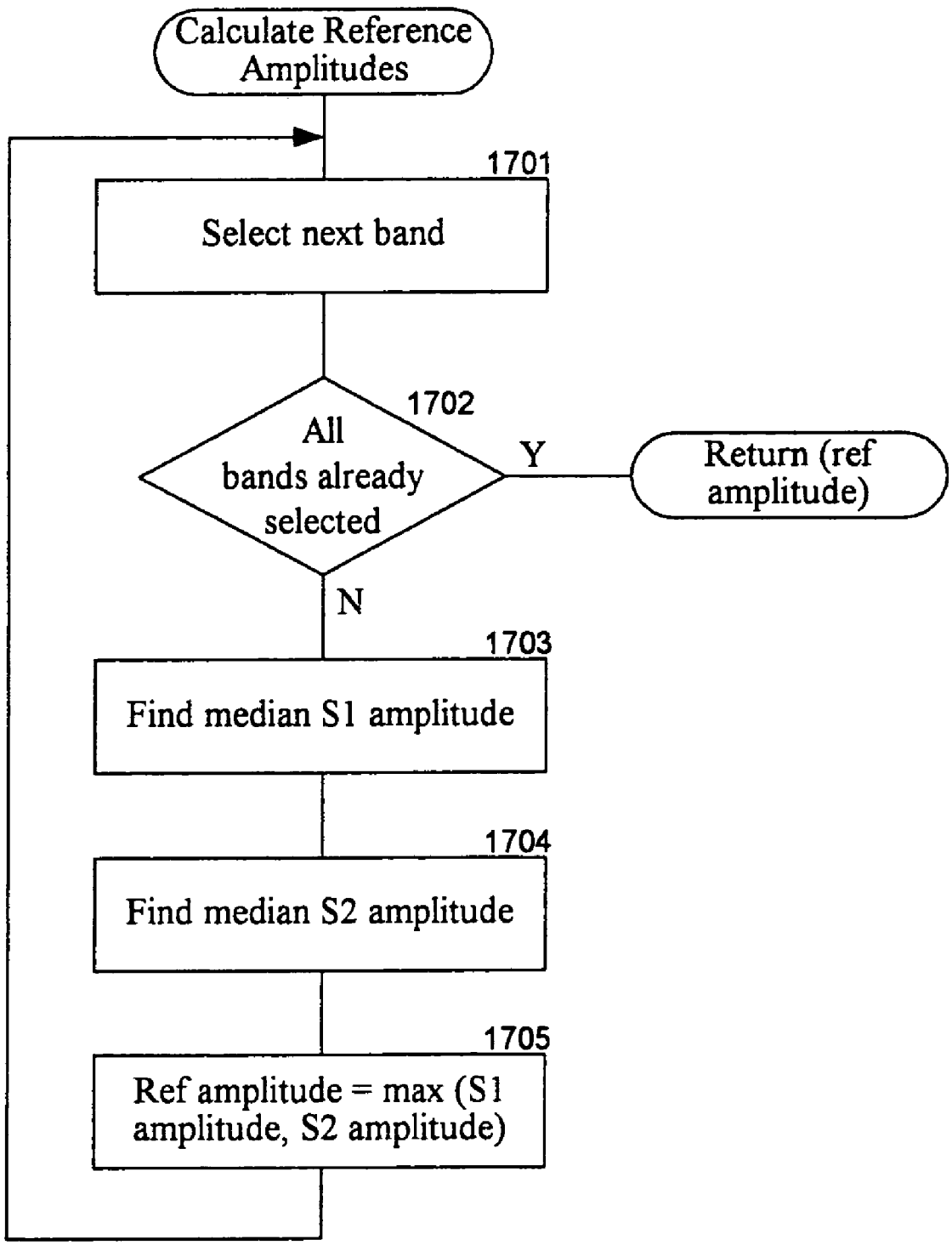
FIG. 17 is a flow diagram illustrating the processing of the calculate reference amplitudes component in one embodiment.

FIG. 17 is a flow diagram illustrating the processing of the calculate reference amplitudes component in one embodiment. The component calculates a reference amplitude for each band. The component identifies the median amplitudes for S1 and S2 and then selects the larger median amplitude as the reference amplitude for the band. In block 1701–1705, the component loops selecting each band and identifying the reference amplitude for that band. In block 1701, the component selects the next band. In decision block 1702, if all the bands have already been selected, then the component returns the reference amplitudes, else the component continues at block 1703. In block 1703, the component identifies the median amplitude within the S1 window of the beats within the selected band. In block 1704, the component identifies the median amplitude within the S2 window of the beats with the selected band. In block 1705, the component calculates the reference amplitude for the selected band as the maximum of the median amplitude for the S1 window (block 1703) and the median amplitude for the S2 window (block 1704). The component then loops to block 1701 to select the next band.

Figure 18:
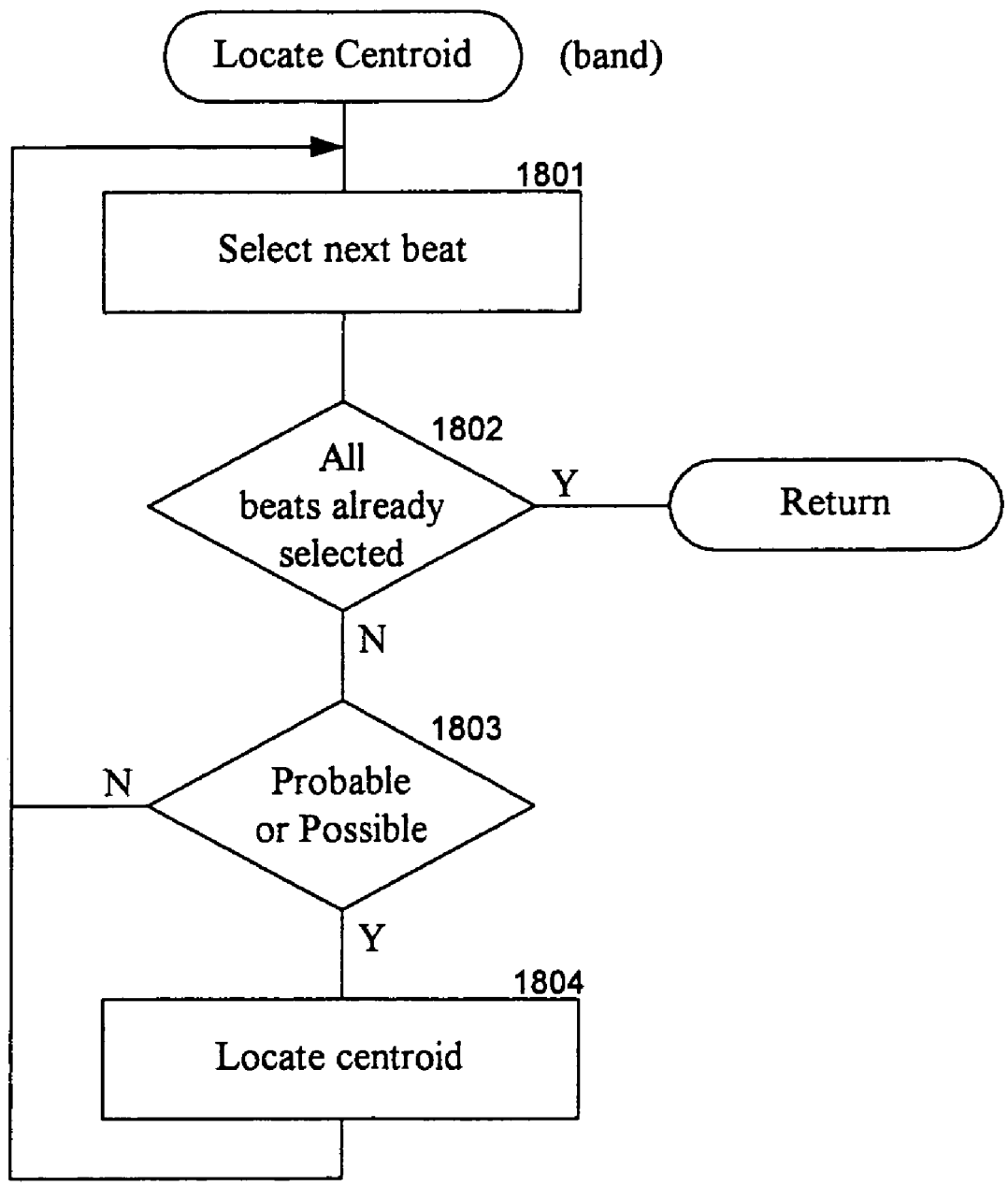
FIG. 18 is a flow diagram illustrating the processing of the calculate centroid component in one embodiment.

FIG. 18 is a flow diagram illustrating the processing of the locate centroid component in one embodiment. The component is invoked to identify the locations of the geometric centroids for S3 and S4. The component is passed an indication of a sound that is to be detected (i.e., S3 or S4) and returns the location of the geometric centroid for that sound. In block 1801, the component selects the next beat. In decision block 1802, if all the beats have already been selected, then the component returns, else the component continues at block 1803. In decision block 1803, if the selected beat has been classified as possible or probable for the passed sound, then the component continues at block

1804, else the component loops to block 1801 to select the next beat. In block 1804, the component identifies the location of the geometric centroid of the sound, for the selected beat within each band and then loops to block 1801 to select the next beat. One skilled in the art will appreciate that many different techniques can be used to calculate an approximation of the geometric centroid.

Figure 19:
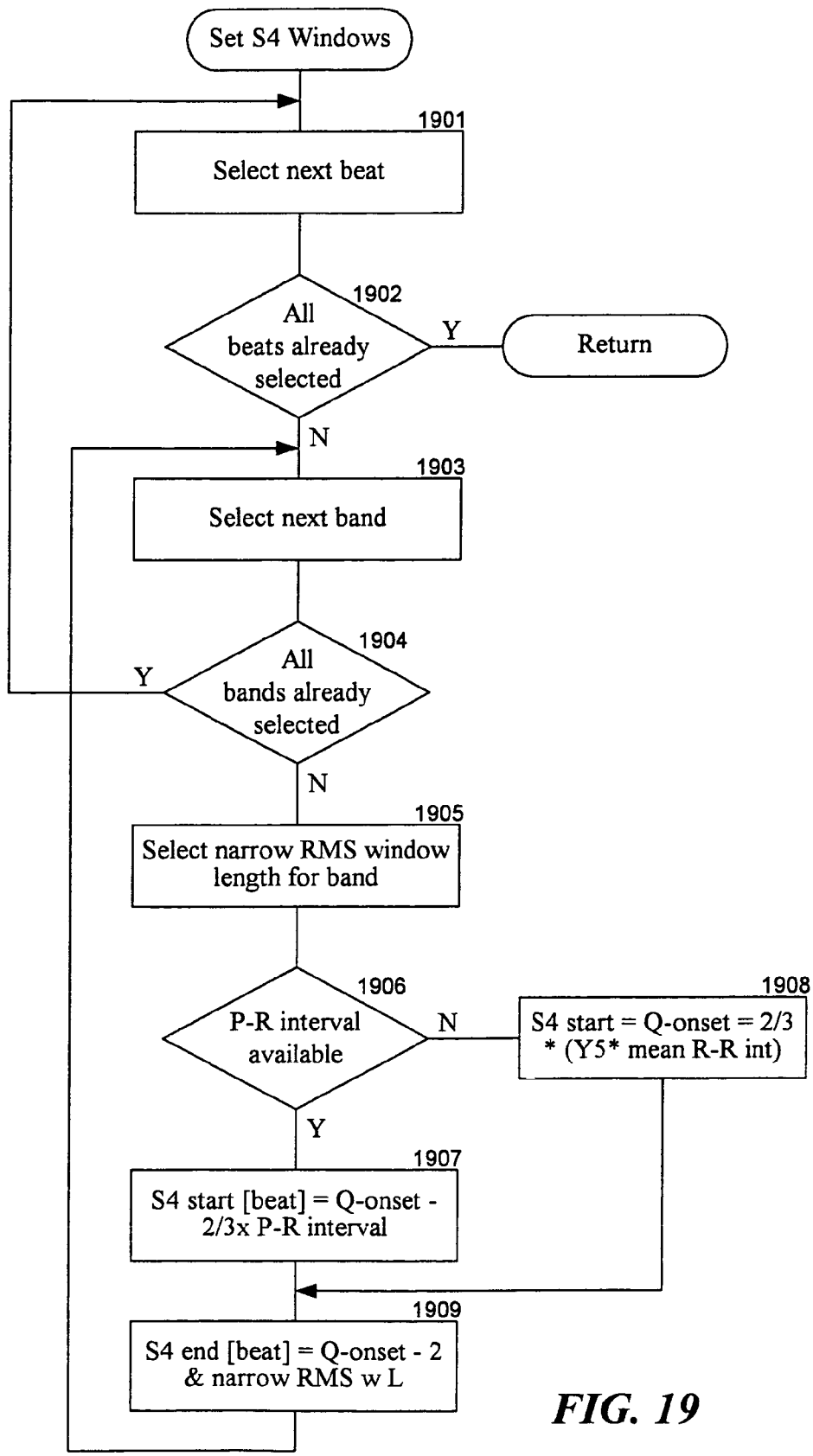
FIG. 19 is a flow diagram illustrating the processing of the set S4 windows component in one embodiment.

FIG. 19 is a flow diagram illustrating the processing of the set S4 windows component in one embodiment. In blocks 1901–1909, the component loops selecting each beat and each band within each beat and setting the S4 window for that beat. In block 1901, the component selects the next beat. In decision block 1902, if all the beats have already been selected, then the component returns, else the component continues at block 1903. In block 1903, the component selects the next band. In decision block 1904, if all the bands have already been selected for the selected beat, then the component loops to block 1901 to select the next beat, else the component continues at block 1905. In block 1905, the component selects the narrow RMS window size for the selected band. In decision block 1906, if the P-R interval for the selected beat has been identified, then the component continues at block 1907, else the component continues at block 1908. In block 1907, the component sets the start of the window for the selected beat to the Q-onset minus ⅔ of the P-R interval. In block 1908, the component sets the start of the beat to Q-onset minus ⅔ of ⅕ of the mean R—R interval. In block 1909, the component sets the end of the beat to the Q-onset minus two times the narrow RMS window size plus a fixed constant such as 0 ms or 20 ms. The component then loops to block 1901 to select the next beat.

Sound Reporting

The sound system generates sound statements based on the sound analysis. The following table lists the criteria and sound statements. If a criteria is satisfied, the sound system outputs the corresponding sound statement.

| Sound Statements | |
|---|---|
| Criteria | Statements |
| Excluder | "{Excluder} detected - analysis for heart sounds not possible" |
| Mean Corr (bands 1, 2, 3) < 0.8 | "Irregular signal" |
| Mean Corr (bands 1, 2, 3) < 0.7 | "Very irregular signal" |
| Mean SNFR (bands 2, 3, 4, 5) < 10 | "Excessive noise - analysis for heart sounds not possible" |
| HR > 115 pm | "Heart rate too high - analysis for heart sounds not possible" |
| Corr (band 1) > 0.85 and Corr (band 3) < 0.7 and SNFR (band 4) < 4 and SNFR (band 2) > 10 | "Possible 50/60 Hz noise - analysis for heart sounds not possible" |
| Corr (band 3) < 0.6 and RMS-heart sounds signal < 10 | "Possible Air Leak - analysis for heart sounds not possible" |
| Mean SNFR (bands 2, 3, 4, 5) > 5 and (Mean Corr (bands 1, 2, 3) > 0.7 or S3 particularly strong) and sum ("Probable" S3s + ½* "Possible" S3s) >= 3 and >= .5 * # valid beats | "S3 detected" |
| Mean SNFR (bands 2, 3, 4, 5) > 5 and (Mean Corr (bands 1, 2, 3) > 0.7 or S4 particularly strong) and sum ("Probable" S4s + ½* "Possible" S4s) >= 3 and >= .5 * # valid beats | "S4 detected" |

ECG Sound/Graph Output

The sound system outputs a sound detection area that includes a graph of the ECG data and sound data for a beat along with an indication of the location of each sound that was detected. The sound system selects a beat that is representative of the S3 and/or S4 detection. The system selects a beat that meets the following conditions:

1. The beat is normal (e.g., not followed by an early or ectopic beat)
2. The beat has a high beat-to-beat correlation
3. S3 and/or S4 were detected in the beat, if S3 and/or S4 was indicated
4. The beat has a large amplitude of S3 and/or S4, if S3 and/or S4 was indicated
5. The beat has the lowest noise in band 5 outside the detection window as defined as follows:
   A. start of beat to start of S1 window
   B. end of S1 window to start of S2 window
   C. end of S2 window to end of beat.

One skilled in the art will appreciate that although specific embodiments of the sound system have been described herein for purposes of illustration, various modifications may be made without deviating from the spirit and scope of the invention. For example, one skilled in the art will appreciate that the system may be adapted to detect sound in an average beat. In generating the average beat, the system may exclude beats that have a low quality (e.g., too much noise) or that have a low beat-to-beat correlation. The system may use an alpha trimming averaging technique to exclude segments of beats that have transient, non-cardiac cycle related noise. One skilled in the art will appreciate that different thresholds and window sizes can be used. For example, the thresholds can be population specific. Accordingly, the invention is defined by the following claims.

We claim:

1. A system for detecting heart sound, comprising:
    a component that filters sound data into frequency bands;
    a component that identifies a frequency band for detection of the heart sound;
    a component that defines a window within each beat of the sound data where the heart sound is expected to be located for heart sounds S1, S2, S3 and S4;
    a component that classifies each beat based on characteristics of the filtered sound data within the defined window of the identified frequency band; and
    a component that indicates the presence of the heart sound based on the classification of the beats.

2. The system of claim 1 wherein the heart sound is an abnormal heart sound and the classification of each beat is based on a reference amplitude derived from a normal sound of the sound data.

3. The system of claim 1 wherein each beat is classified as invalid, not having the heart sound, possibly having the heart sound, or probably having the heart sound.

4. The system of claim 3 wherein the presence of the heart sound is indicated based on number of beats classified as possibly or probably having the heart sound relative to the number of beats not having a heart sound.

5. The system of claim 1 wherein the identification of the frequency band is based on analysis of signal-to-noise floor ratio of the filtered sound data.

6. A computer-readable medium containing instructions for controlling a computer system to detect an abnormal heart sound by a method comprising:
    filtering sound data into frequency bands;
    identifying a frequency band for detection of the heart sound;
    defining a window within each beat of the sound data where the heart sound is expected to be located for heart sounds S1, S2, S3 and S4;

classifying each beat based on characteristics of the filtered sound data within the defined window of the identified frequency band;

indicating the presence of the heart sound based on the classification of the beats;

wherein, if the heart sound is an abnormal heart sound, the classification of each beat is based on a reference amplitude derived from a normal sound of the sound data.

7. The computer-readable medium of claim 6 including determining the location of the heart sound within a beat.

8. The computer-readable medium of claim 7 including displaying an indication of the location of the heart sound relative to a beat.

9. The computer-readable medium of claim 6 wherein the defining of the window uses ECG data.

10. A method for detecting a selected heart sound comprising receiving, during a selected common time interval, both ECG and heart-sound data, characterizing, by filtering, the heart-sound data for heart sounds S1, S2, S3 and S4 in different, selected frequency bands, applying, for the selected heart sound, an appropriate temporal window to the frequency band information, analyzing the band information present in the window, and using the results of said analyzing to indicate the presence or absence of the selected heart sound.

* * * * *